(12) United States Patent
Wong et al.

(10) Patent No.: US 9,561,223 B2
(45) Date of Patent: *Feb. 7, 2017

(54) GROUP OF ALKALOIDS, THE NOVEL AUTOPHAGIC ENHANCERS FOR TREATMENT OF CANCERS AND NEURODEGENERATIVE CONDITIONS THEREOF

(71) Applicant: Macau University of Science and Technology, Macau (CN)

(72) Inventors: Kam Wai Wong, Macau (CN); Yuen Kwan Law, Macau (CN); Liang Liu, Macau (CN); Jingrong Wang, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,420

(22) Filed: Dec. 31, 2015

(65) Prior Publication Data
US 2016/0106734 A1    Apr. 21, 2016

Related U.S. Application Data

(62) Division of application No. 14/562,781, filed on Dec. 8, 2014.

(60) Provisional application No. 61/923,231, filed on Jan. 3, 2014.

(51) Int. Cl.
*A61K 31/4725* (2006.01)
*A61K 31/4745* (2006.01)
*A61K 31/4748* (2006.01)

(52) U.S. Cl.
CPC ....... *A61K 31/4745* (2013.01); *A61K 31/4725* (2013.01); *A61K 31/4748* (2013.01)

(58) Field of Classification Search
IPC .................................................. A61K 31/4725
See application file for complete search history.

(56) References Cited

U.S. PATENT DOCUMENTS 6,841,560 B2 *   1/2005  Thompson ........... C07D 217/02
                                                       514/310
2001/0055630 A1 * 12/2001  Castillo ................ A61K 31/215
                                                       424/769

* cited by examiner

*Primary Examiner* — Shirley V Gembeh
(74) *Attorney, Agent, or Firm* — Eagle IP Limited; Jacqueline C. Lui

(57) ABSTRACT

The present invention discloses a method of treating cancer comprising administering an effective amount of an alkaloid, in which the alkaloid is liensinine, isoliensinine, dauricine, cepharanthine, hernandezine or thalidezine and isolated from the traditional Chinese medicinal herbs. The use of the alkaloid in treating neurodegenerative disorder is also disclosed.

3 Claims, 21 Drawing Sheets

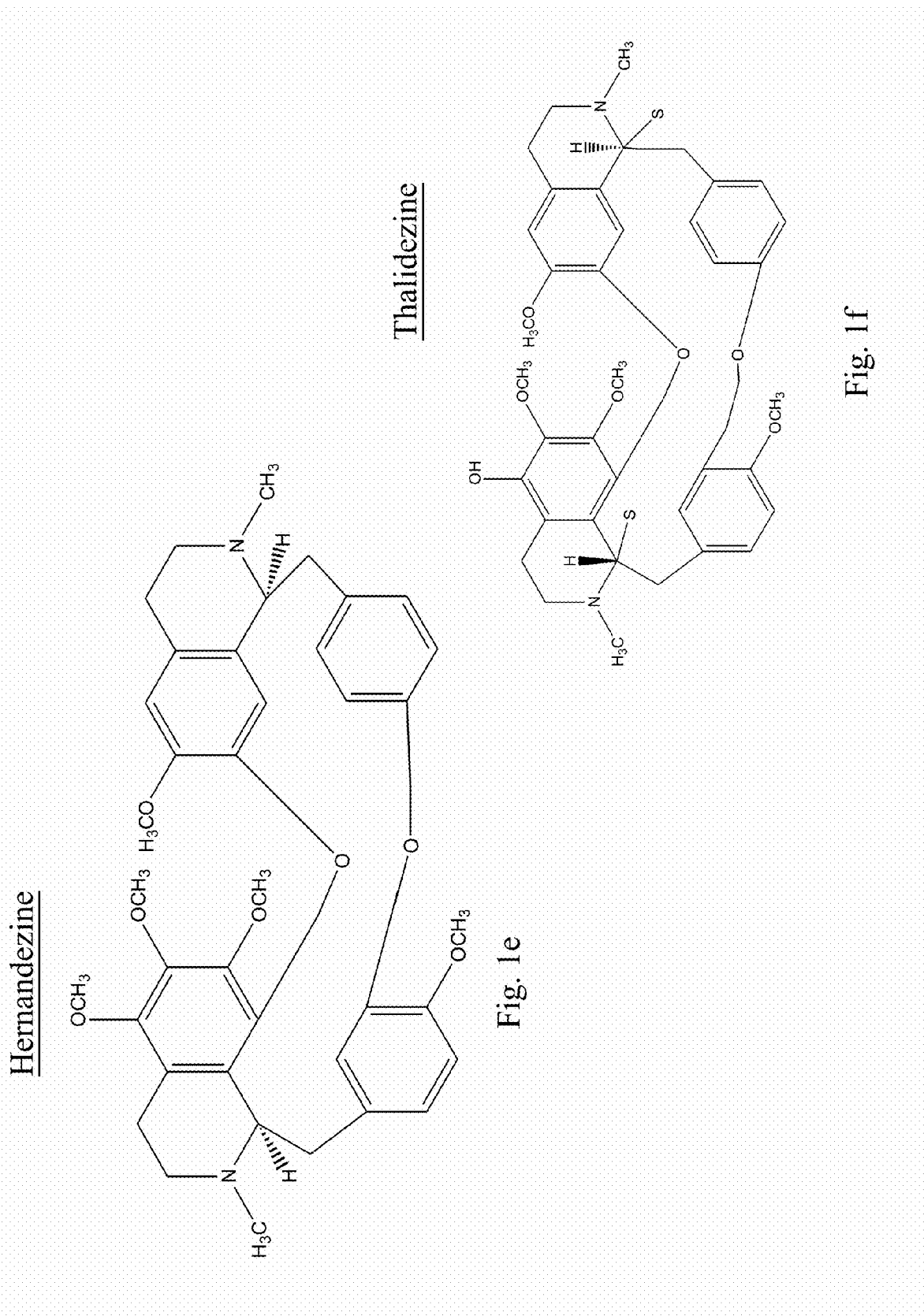
Fig. 1e Hernandezine
Fig. 1f Thalidezine

| Cell types | Liensinine (μM) | Isoliensinine (μM) | Dauricine (μM) | Cepharanthine (μM) | Hernandezine (μM) | Thalidezine (μM) |
|---|---|---|---|---|---|---|
| HeLa (Cervical) | 32.4 | 15.8 | 14.5 | 8.9 | 14.8 | 14.8 |
| A549 (Lung) | 60 | 31.1 | 40.4 | 32.4 | 7.59 | 7.47 |
| MCF-7 (Breast) | 61.8 | 26.4 | 28.7 | 13.8 | 14 | 9.9 |
| PC3 (Prostate) | 33.5 | 21.4 | 27 | 11.5 | 11.4 | 13.1 |
| HepG2 (Liver) | 15.5 | 12.2 | 16.7 | 7.06 | 7.42 | 10.6 |
| Hep3B (Liver) | 10.2 | 4.52 | 13.9 | 5.64 | 6.71 | 8.07 |
| H 1299 (Lung) | 19.4 | 9.7 | 6.18 | 7.1 | 6.74 | 7.47 |
| LO2 (Liver-normal) | >100 | 55.8 | 65.1 | 61.2 | 65.1 | 88.4 |

Fig. 1g

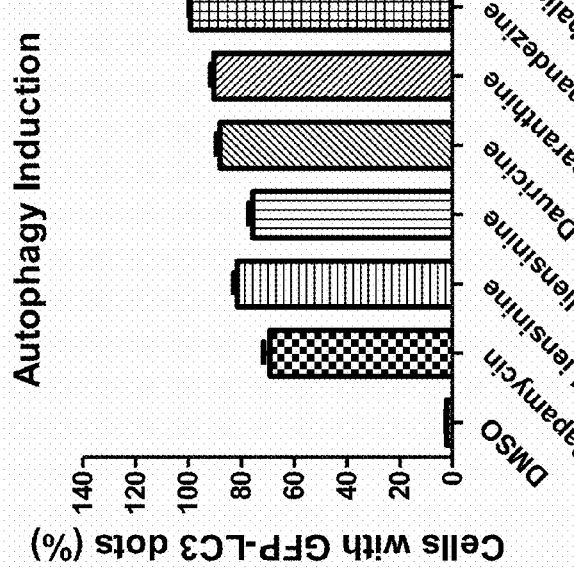
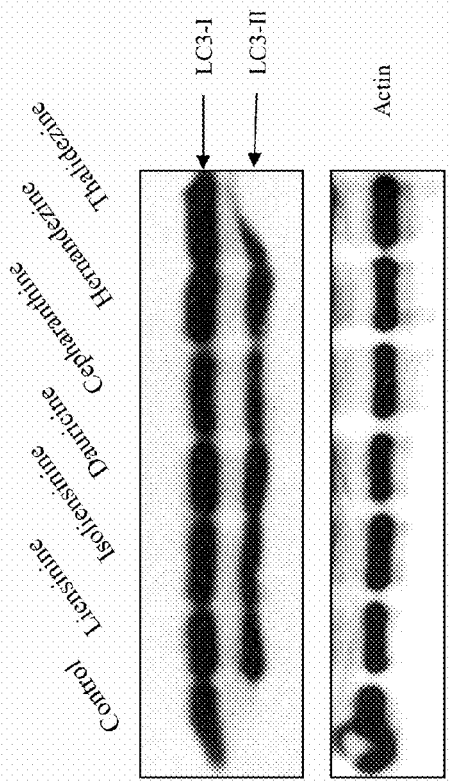
Fig. 2a
Fig. 2b

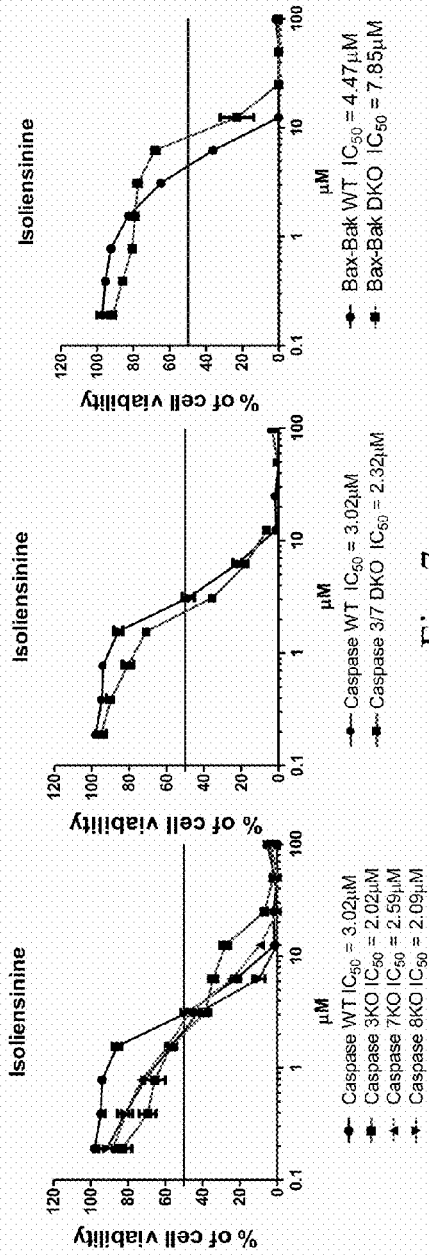
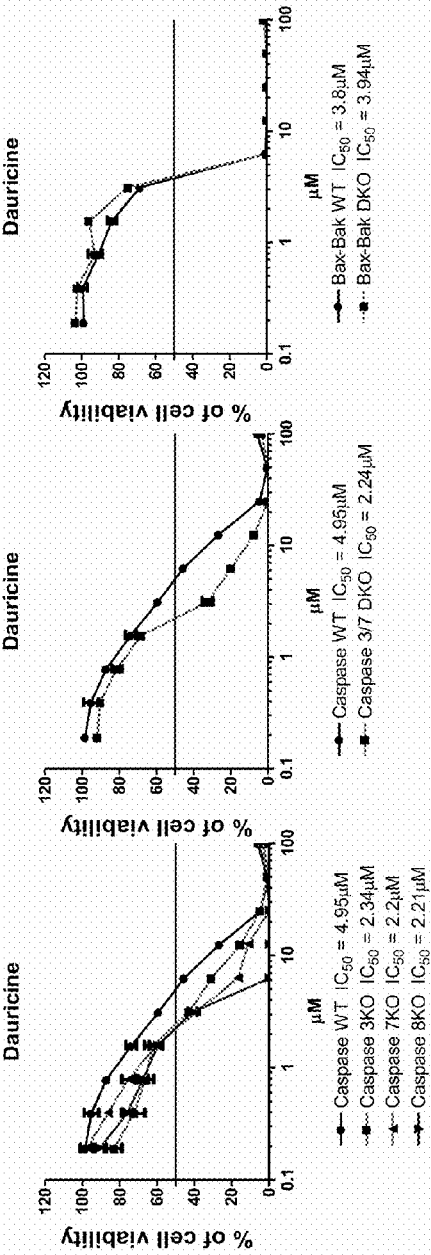
Fig. 7a
Fig. 7b

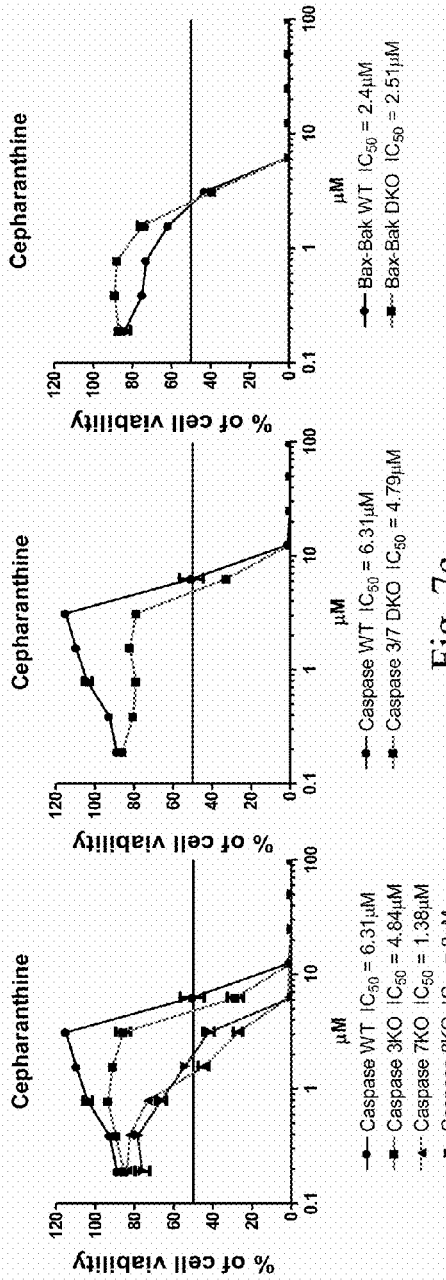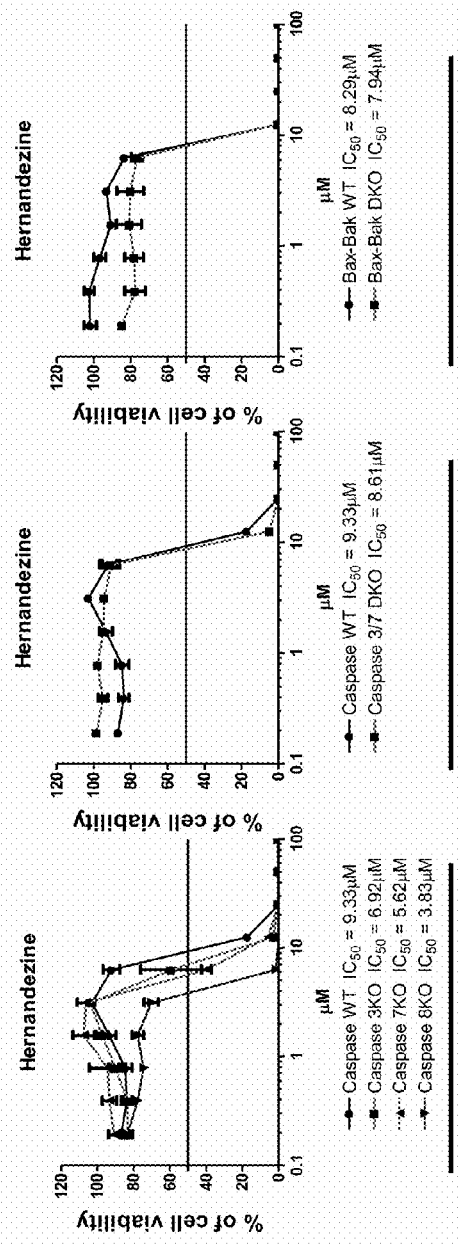
Fig. 7c
Fig. 7d

GROUP OF ALKALOIDS, THE NOVEL AUTOPHAGIC ENHANCERS FOR TREATMENT OF CANCERS AND NEURODEGENERATIVE CONDITIONS THEREOF

CROSS-REFERENCE TO RELATED APPLICATION

This application is a divisional application of U.S. Ser. No. 14/562,781 filed on 8 Dec. 2014, which claims benefit under 35 U.S.C. §119(e) of U.S. Provisional Application having Ser. No. 61/923,231 filed 3 Jan. 2014, which is hereby incorporated by reference herein in its entirety.

FIELD OF INVENTION

This invention relates to a group of novel autophagy enhancers, namely liensinine, isoliensinine, dauricine, cepharanthine, hernandezine and thalidezine, and their use thereof in treating cancers and neurodegenerative conditions.

BACKGROUND OF INVENTION

Autophagy is a cellular degradation process that involves the delivery of cytoplasmic cargo such as long-lived protein, mis-folded protein or damaged organelles, sequestered inside double-membrane vesicles (autophagosome) before entering lysosome for degradation. Autophagy occurs at low basal levels in cells to maintain normal homeostatic functions by turnover of proteins and organelles. Upon cellular stressful conditions such as nutrient deprivation, oxidative stress, infection or protein aggregate accumulation, autophagy starts with membrane isolation and expansion to form autophagosome that sequesters all unwanted cytoplasmic materials. Followed by fusion of the autophagosome with lysosome to form an autolysosome, all the engulfed materials are degraded to recycle intracellular nutrients and energy [1]. Both autophagy impairment and the age-related decline of autophagic function lead to the pathogenesis of many age-related diseases such as neurodegenerative disorders and cancers [2].

One of the key roles for autophagy is to degrade toxic aggregate-prone cytoplasmic proteins that are inaccessible to the proteasome when they form oligomers or aggregates [3]; aggregate-prone proteins with polyglutamine and polyalanine expansions, in turn, are degraded by autophagy [4]. Inhibition of mTOR induces autophagy and reduces toxicity of polyglutamine expansions or mutant proteins in fly and mouse models [4-7]. These mutant proteins include mutant α-synuclein which causes Parkinson's disease, and polyglutamine-expanded mutant huntingtin that causes Huntington's disease [8,9]. In contrast, protein aggregates form in the cytoplasm when autophagy is inhibited in normal mice [10]. Rapamycin, a United States Food and Drug Administration (FDA)-approved immunosuppressant, is found effective in treating fruit fly and mouse models of Huntington's disease through increased autophagic clearance of mutant huntingtin [5]. Besides, a small-molecule screen also revealed new chemicals that attenuate the toxicity of mutant huntingtin through autophagy [9].

While autophagy may play a protective role in neurodegenerative diseases [9], autophagic dysfunction is associated with DNA damage, chromosome instability [11, 12], and increased incidence of malignancies [12]. Modulators of autophagy may play a protective role through promoting autophagic cell death in tumors or augmenting the efficacy of chemotherapeutic agents when used in combination. Several clinically approved or experimental antitumor agents induced autophagy-related cell death in various types of cancer cells [13-16].

Recently, natural compounds from alkaloids have been found to induce autophagy with potential neuroprotective or anti-cancer effects. For instance, alkaloids isolated from Chinese herbal medicine are important source for drug discovery [17]. Alkaloids such as berberine, matrine and tetrandrine, exhibit their anti-cancer effects through cell cycle arrest, apoptosis, autophagy, inhibition of metastasis or angiogenesis [18-20]. Camptothecin and vinblastine are chemotherapeutic drugs that have been approved for clinical use [21,22]. In addition, alkaloids such as isorhynchophylline [23] and berberine were also reported for their neuroprotective effects in vitro.

SUMMARY OF INVENTION

In the light of the foregoing background, it is an object of the present invention to provide the alternate alkaloids as novel autophagy enhancers with their potential therapeutic application in cancers and neurodegenerative diseases by induction of autophagy-related cell death in a panel of cancer cells and clearance of mutant huntingtin in neuronal cells. In one embodiment, such alkaloids include liensinine, isoliensinine, dauricine, cepharanthine, hernandezine and thalidezine.

Accordingly, the present invention, in one aspect, is a method of treating cancer including administering an effective amount of an alkaloid to a subject in need thereof, wherein the alkaloid is isoquinoline alkaloid, bisbenzylisoquinoline alkaloid, biscoclaurine alkaloid or bisisoquinoline alkaloid.

In one exemplary embodiment, the isoquinoline alkaloid is liensinine; the bisbenzylisoquinoline alkaloid is isoliensinine, dauricine or hernandezine; the biscoclaurine alkaloid is cepharanthine; and the bisisoquinoline alkaloid is thalidezine.

In an exemplary embodiment, the cancer is cervical cancer, breast cancer, liver cancer, lung cancer or prostate cancer.

In another exemplary embodiment, the alkaloid exhibits specific cytotoxic effect towards a panel of human cancer cells.

In another exemplary embodiment, cancer is treatable by alkaloids-mediated autophagy; in a further exemplary embodiment, the alkaloids-mediated autophagy is autophagy-related gene 7 dependent.

In an exemplary embodiment, the cancer is caused by and/or originated from cells containing wild-type autophagy-related gene 7, and is treated by administering liensinine, isoliensinine, dauricine, cepharanthine, hernandezine and/or thalidezine to a subject in need thereof.

In yet another exemplary embodiment, the cancer is caused by and/or originated from apoptosis-resistant cells, and is treated by administering isoliensinine, dauricine, cepharanthine, hernandezine and thalidezine to a subject in need thereof.

According to another aspect of the present invention, a pharmaceutical composition for treating cancer comprising an alkaloid is provided, in which the alkaloid is isoquinoline alkaloid, bisbenzylisoquinoline alkaloid, biscoclaurine alkaloid or bisisoquinoline alkaloid.

In one exemplary embodiment, the isoquinoline alkaloid is liensinine; the bisbenzylisoquinoline alkaloid is isoliensinine, dauricine or hernandezine; the biscoclaurine alkaloid is cepharanthine; and the bisisoquinoline alkaloid is thalidezine.

In an exemplary embodiment, the cancer is cervical cancer, breast cancer, liver cancer, lung cancer or prostate cancer.

In another exemplary embodiment, cancer is treatable by alkaloids-mediated autophagy; in a further exemplary embodiment, the alkaloids-mediated autophagy is autophagy-related gene 7 dependent.

In a further aspect of the present invention, a method of treating neurodegenerative disorder including administering an effective amount of an alkaloid to a subject in need thereof is provided, in which the alkaloid is isoquinoline alkaloid, bisbenzylisoquinoline alkaloid, biscoclaurine alkaloid or bisisoquinoline alkaloid.

In one exemplary embodiment, the isoquinoline alkaloid is liensinine; the bisbenzylisoquinoline alkaloid is isoliensinine, dauricine or hernandezine; the biscoclaurine alkaloid is cepharanthine; and the bisisoquinoline alkaloid is thalidezine.

In an exemplary embodiment, the neurodegenerative disorder is caused by cells containing mutant huntingtin HDQ55/74.

In another exemplary embodiment, the neurodegenerative disorder is Huntington's disease.

In another aspect of the present invention, a pharmaceutical composition for treating neurodegenerative disorder comprising an alkaloid is provided, in which the alkaloid is isoquinoline alkaloid, bisbenzylisoquinoline alkaloid, biscoclaurine alkaloid or bisisoquinoline alkaloid.

In one exemplary embodiment, the isoquinoline alkaloid is liensinine; the bisbenzylisoquinoline alkaloid is isoliensinine, dauricine or hernandezine; the biscoclaurine alkaloid is cepharanthine; and the bisisoquinoline alkaloid is thalidezine.

In an exemplary embodiment, the neurodegenerative disorder is caused by cells containing mutant huntingtin HDQ55/74.

In another exemplary embodiment, the neurodegenerative disorder is Huntington's disease.

BRIEF DESCRIPTION OF FIGURES

FIGS. 1a to 1f show the chemical structures of liensinine, isoliensinine, dauricine, cepharanthine, hernandezine and thalidezine.

FIG. 1g shows the results of cell cytotoxicity study of liensinine, isoliensinine, dauricine, cepharanthine, hernandezine and thalidezine towards a panel of cancer and normal cells.

FIGS. 2a to 2b show that liensinine, isoliensinine, dauricine, cepharanthine, hernandezine and thalidezine induce autophagic GFP-LC3 puncta formation and autophagic protein LC3-II conversion in HeLa cancer cells.

FIGS. 7a to 7e show that isoliensinine, dauricine, cepharanthine, hernandezine and thalidezine are able to induce cell death in apoptosis-resistant cells.

DETAILED DESCRIPTION OF THE PREFERRED EMBODIMENTS

Figure 1A:
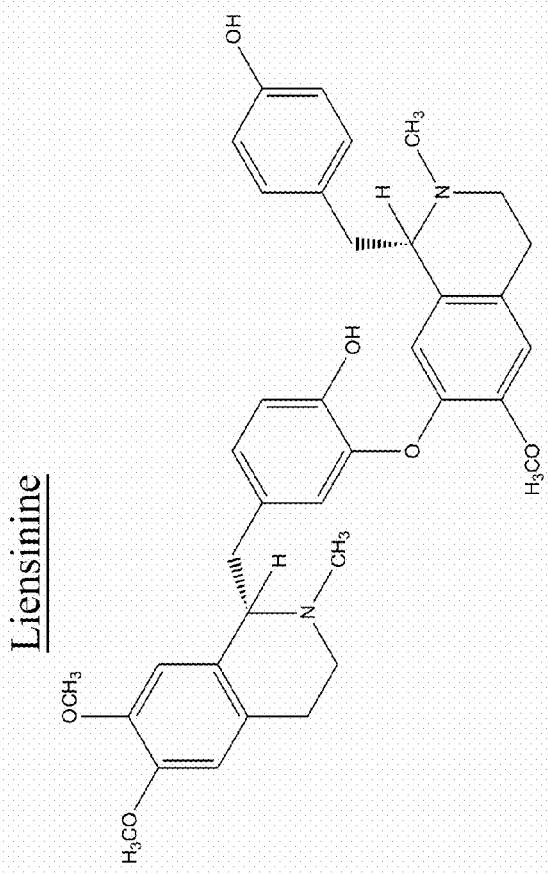
Figure 1B:
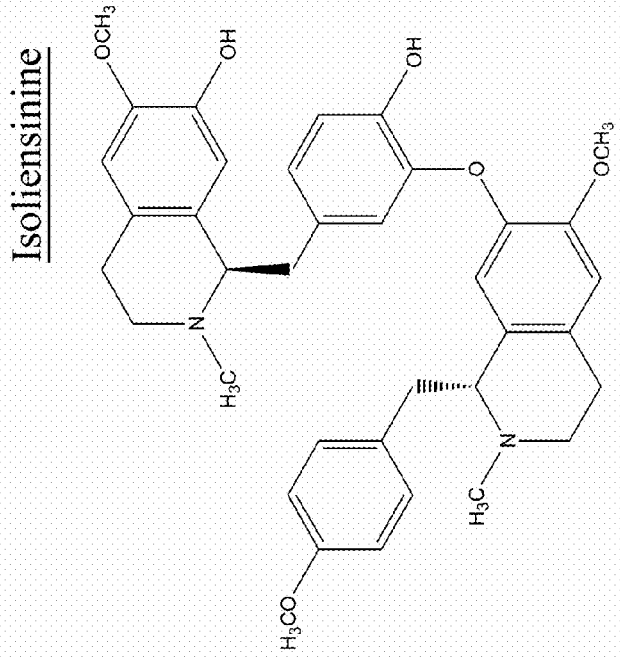
Figure 1D:
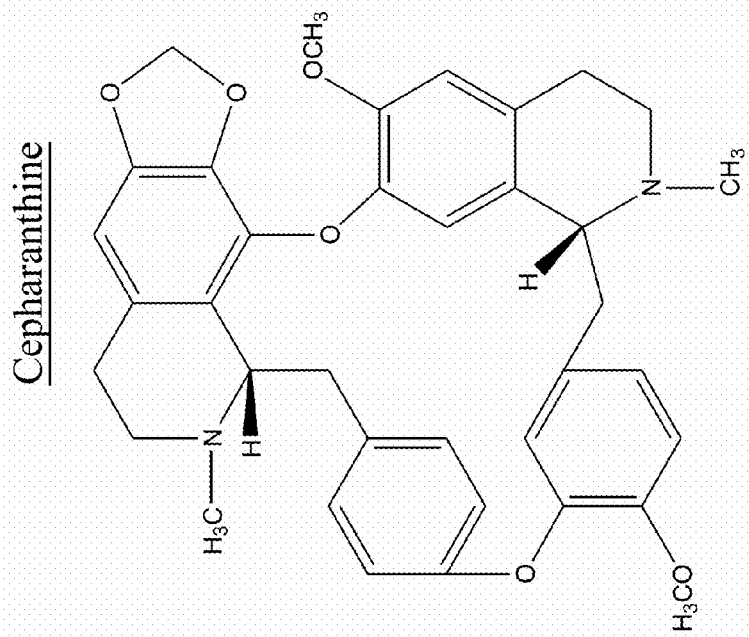
Figure 1C:
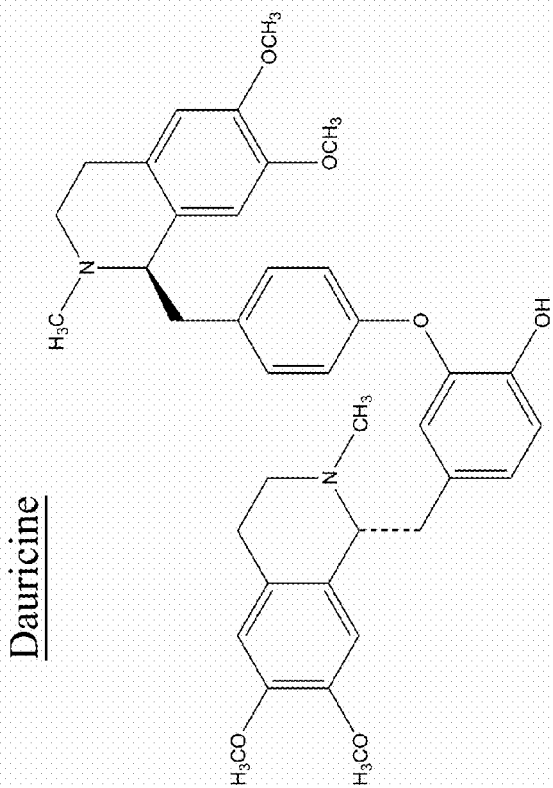

As used herein and in the claims, "comprising" means including the following elements but not excluding others.

In this invention, a group of alkaloids including liensinine, isoliensinine, dauricine, cepharanthine, hernandezine and thalidezine are identified as novel inducers of autophagy. The chemical structures of these six alkaloids are demonstrated in FIGS. 1a to 1f respectively. Studies conducted by inventors demonstrate that liensinine, isoliensinine, dauricine, cepharanthine, hernandezine and thalidezine can induce autophagy and autophagic cell death in a panel of cancer and apoptosis-resistant cells. On the other hand, these compounds are capable of promoting the degradation of mutant huntingtin with HDQ55 or 74 CAG repeats in PC12 cells. Taken together, works by the inventors provide novel insights into the autophagic effect of selected alkaloids and their potential uses in anti-tumor or neuroprotective therapy in future.

Furthermore, in this invention, liensinine and isoliensinine are derived and isolated from seed embryos of *Nelumbo nucifera*; dauricine is derived and isolated from *Asiatic Moonseed Rhizome*; cepharanthine is derived and isolated from *Stephania cepharantha*; and hernandezine and thalidezine are derived and isolated from *Thalictrum podocarpum Humb*.

The following preparations and examples are given to enable those skilled in the art to more clearly understand and to practice the present invention. They should not be considered as limiting the scope of the invention, but merely as being illustrative and representative thereof.

Example 1

Study on Cell Cytotoxicity

This example describes in vitro cell cytotoxicity of liensinine, isoliensinine, dauricine, cepharanthine, hernandezine and thalidezine in a panel of human cancer and normal cells.

1.1 Cell Culture and Cytotoxicity Assay.

The test compounds of liensinine, isoliensinine, dauricine, cepharanthine, hernandezine and thalidezine were dissolved in DMSO at a final concentration of 100 mmol/L and stored at −20° C. Cytotoxicity was assessed using the 3-(4,5-dimethylthiazol-2-yl)-2,5-diphenyltetrazolium bromide assay as described previously [25]. 4000-8000 HeLa (human cervical cancer), MCF-7 (human breast cancer), HepG2 (human liver cancer), Hep3B (human liver cancer), H1299 (human lung cancer), A549 (human lung cancer), PC3 (human prostate cancer) and LO2 (human normal liver) cells were seeded on 96-well plates per well. After overnight pre-incubation, the cells were exposed to different concentrations of liensinine, isoliensinine, dauricine, cepharanthine, hernandezine and thalidezine (0.039-100 μmol/L) for 3 days. Specifically, the following concentrations are used for all of the above alkaloids: 100, 50, 25, 12.5, 6.25, 3.125, 1.5625, 0.78, 0.39, 0.195, 0.079, 0.039 ninon. Subsequently, 10 μL of MTT reagents was added to each well and incubated at 37° C. for 4 hours followed by the addition of 100 μL solubilization buffer (10% SDS in 0.01 mol/L HCl) and overnight incubation. Absorbance at 585 nm was determined from each well on the following day. The percentage of cell viability was calculated using the following formula: Cell viability (%)=Cells number treated/Cells number DMSO control×100. Data was obtained from three independent experiments.

1.2 Results:

As shown in FIG. 1g, significant cell cytotoxicity was observed with mean $IC_{50}$ value ranging from 4.52-61.8 μM observed in a panel of human cancer cells treated with liensinine, isoliensinine, dauricine, cepharanthine, hernandezine and thalidezine for 72 hours as revealed by MTT assay. However, the test compounds of liensinine, isoliensinine, dauricine, cepharanthine, hernandezine and thalidezine indicated no or insignificant cytotoxic effect toward human normal liver LO2 cells.

Example 2

Study on Autophagic Effect

This example describes an in vitro study to demonstrate the autophagic effect of liensinine, isoliensinine, dauricine, cepharanthine, hernandezine and thalidezine.

2.1 Quantification of Autophagy GFP-LC3 Puncta.

GFP-LC3 puncta formation was quantified as previously described [15]. In brief, GFP-LC3 transfected cells grown on coverslips in a 6-well plate were treated with or without 20 μM of liensinine, 10 μM of isoliensinine, dauricine, cepharanthine, hernandezine or thalidezine for 4 hours, the cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

2.2 Detection of Autophagic Marker Protein LC3 Conversion.

After treatments with liensinine, isoliensinine, dauricine, cepharanthine, hernandezine and thalidezine, cells were harvested and lysed in RIPA buffer (Cell Signaling Technologies Inc., Beverly, Mass.). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with LC3 primary antibodies (1:1000) in TBST overnight at 4° C. After that, the membrane was further incubated with HRP-conjugated secondary antibodies for 60 minutes. Finally, protein bands were visualized by using the ECL Western Blotting Detection Reagents (Invitrogen, Paisley, Scotland, UK).

2.3 Quantification of Liensinine, Isoliensinine, Dauricine, Cepharanthine, Hernandezine and Thalidezine-Mediated Autophagy in the Presence of Autophagic Inhibitor.

GFP-LC3 puncta formation was quantified as previously described [15]. In brief, HeLa cells expressing GFP-LC3 were treated with 20 μM of liensinine, or 10 μM of isoliensinine, dauricine, cepharanthine, hernandezine or thalidezine in the presence of autophagic inhibitor, 3-methyl adenine (3-MA, 5 mM), for 4 hours. The cells were then fixed in 4% paraformaldehyde for 20 minutes at room temperature and then rinsed with PBS. Slides were mounted with FluorSave™ mounting media (Calbiochem) and examined by fluorescence microscopy. To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields were scored.

2.4 Results.

Figure 2C:
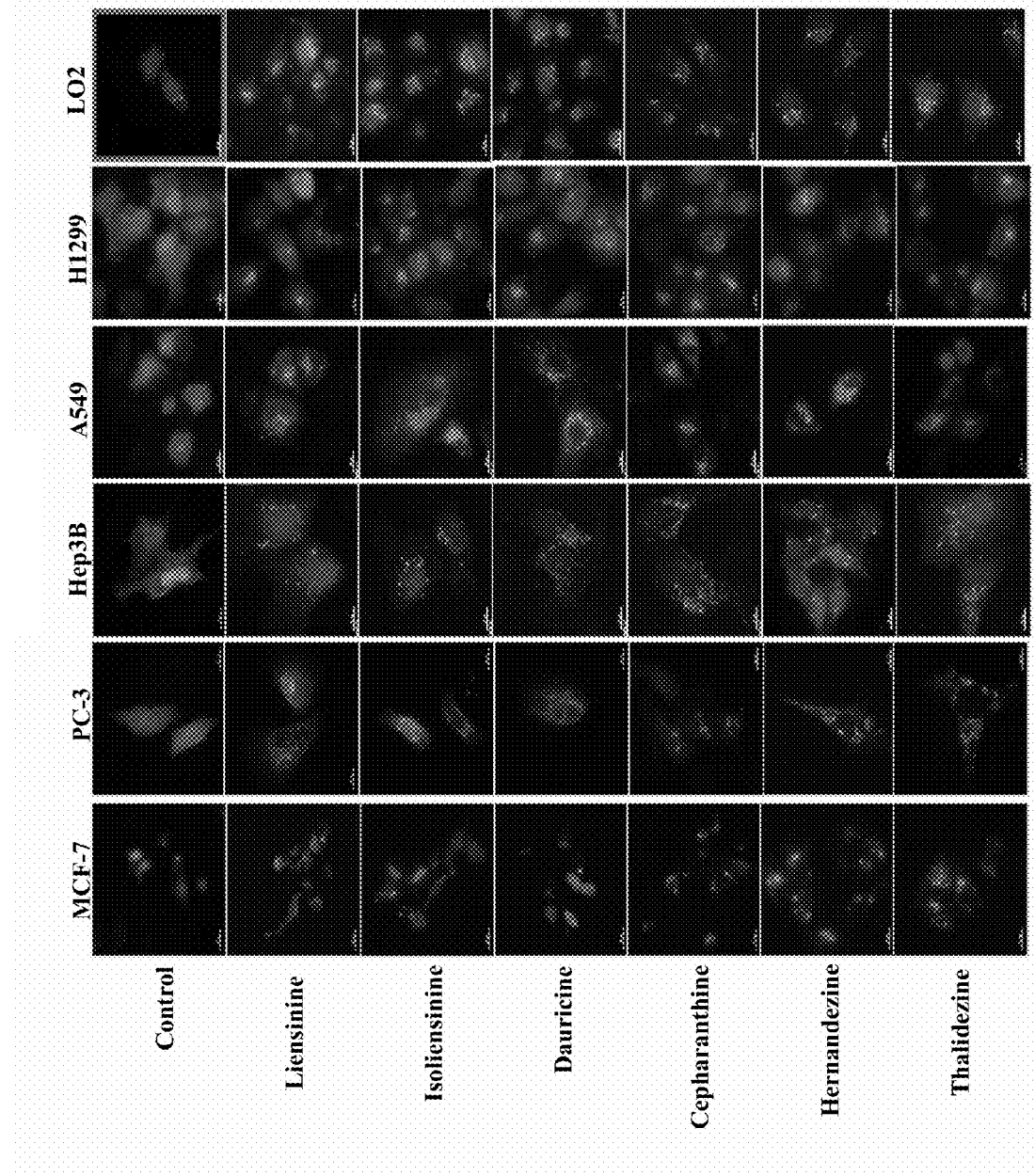
FIG. 2c shows that liensinine, isoliensinine, dauricine, cepharanthine, hernandezine and thalidezine induce autophagic GFP-LC3 puncta formation in a panel of cancer cells.
Figure 3:
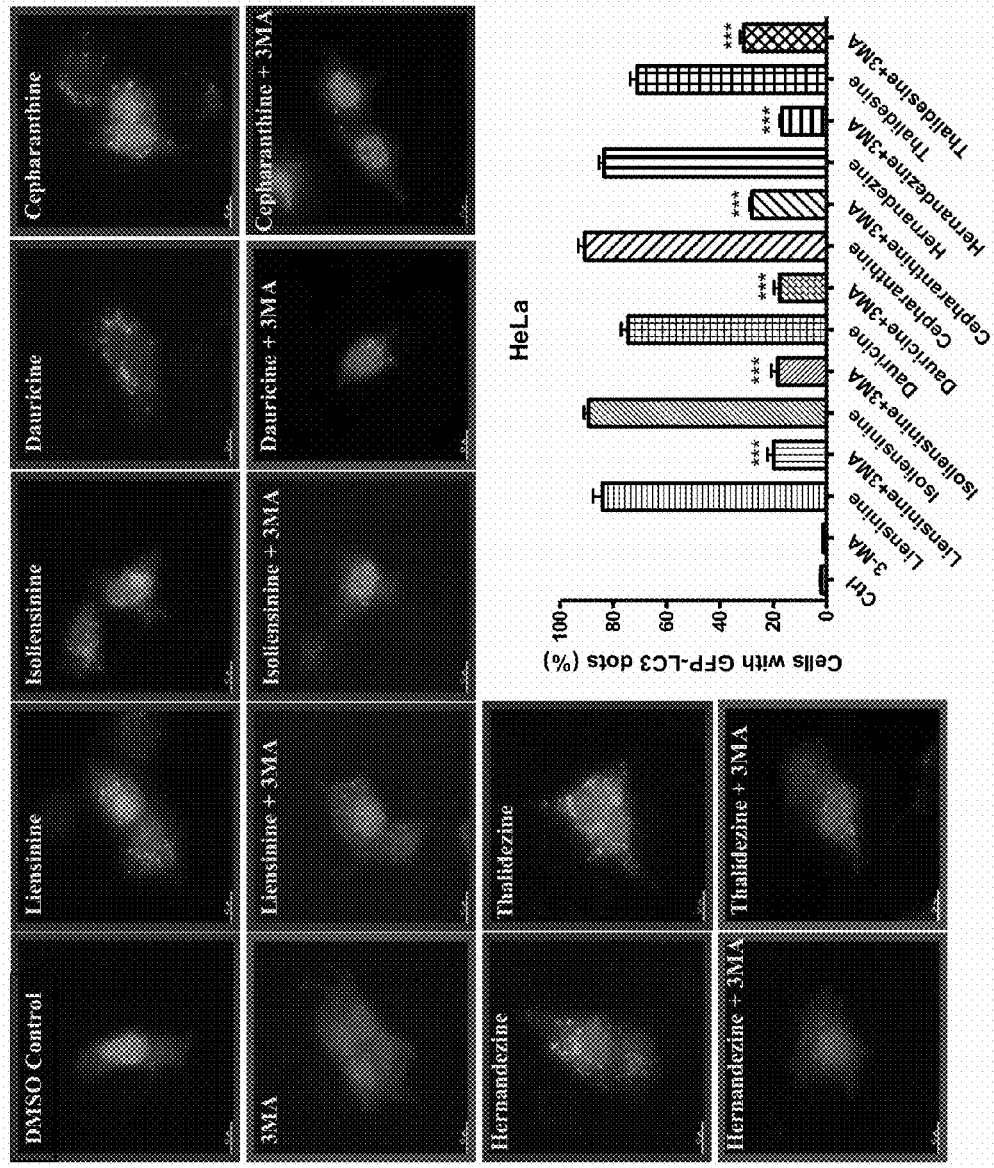
FIG. 3 shows that liensinine, isoliensinine, dauricine, cepharanthine, hernandezine and thalidezine-induced autophagy are abrogated by autophagic inhibitor, 3-methyladenine (3-MA) in HeLa cancer cells.

As compared to DMSO control treatment, liensinine, isoliensinine, dauricine, cepharanthine, hernandezine and thalidezine significantly induced the GFP-LC3 puncta formation in HeLa cancer cells as shown in FIG. 2a. Western blot analysis showed that conversion of the autophagic marker LC3-II was also induced upon treatments of liensinine, isoliensinine, dauricine, cepharanthine, hernandezine and thalidezine as shown in FIG. 2b. In addition, liensinine, isoliensinine, dauricine, cepharanthine, hernandezine and thalidezine also increased the formation of GFP-LC3 puncta towards a panel of cancer and normal cells as revealed by fluorescent microscopy as shown in FIG. 2c. However, there was a significant reduction in the liensinine, isoliensinine, dauricine, cepharanthine, hernandezine and thalidezine-autophagy induced by GFP-LC3 puncta formation in HeLa cells in the presence of autophagic inhibitor (3-MA) as shown in FIG. 3, in which such findings were consistent with the GFP-LC3 puncta formation and LC3 conversion from LC3-I to LC3-II as shown in FIGS. 2a to 2c.

2.5 Conclusion.

The data of this study suggested that liensinine, isoliensinine, dauricine, cepharanthine, hernandezine and thalidezine are the novel autophagy enhancers. Although these compounds could induce autophagy in LO2 human normal liver cells, autophagy mediated by these compounds exhibits far less toxic in human normal liver cells as shown in FIG. 1g, suggesting that the cytotoxic effect mediated by liensinine, isoliensinine, dauricine, cepharanthine, hernandezine or thalidezine is tumor specific.

Example 3

Study on Dependency of the Presence of Autophagy-Related Gene 7 (Atg7) on Autophagic Effect This example describes an in vitro study to demonstrate that the autophagic effect of liensinine, isoliensinine, dauricine, cepharanthine, hernandezine and thalidezine is dependent on the presence of autophagy-related gene 7 (Atg7).

3.1 Quantification of Autophagy GFP-LC3 Puncta in Atg7 Wild Type and Deficient MEFs.

GFP-LC3 puncta formation was quantified as previously described [15]. In brief, both Atg7 wild-type (Atg7-wt or Atg7+/+) and deficient (Atg7−/−) mouse embryonic fibroblasts (MEFs) were transfected with GFP-LC3 plasmid and then grown on coverslips in a 6-well plate. The cells were then treated with 20 μM of liensinine, 10 μM of isoliensinine, 10 μM of dauricine, 10 μM of cepharanthine, hernandezine or 10 μM of thalidezine. for 24 h. The cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields were scored.

Figure 4A:
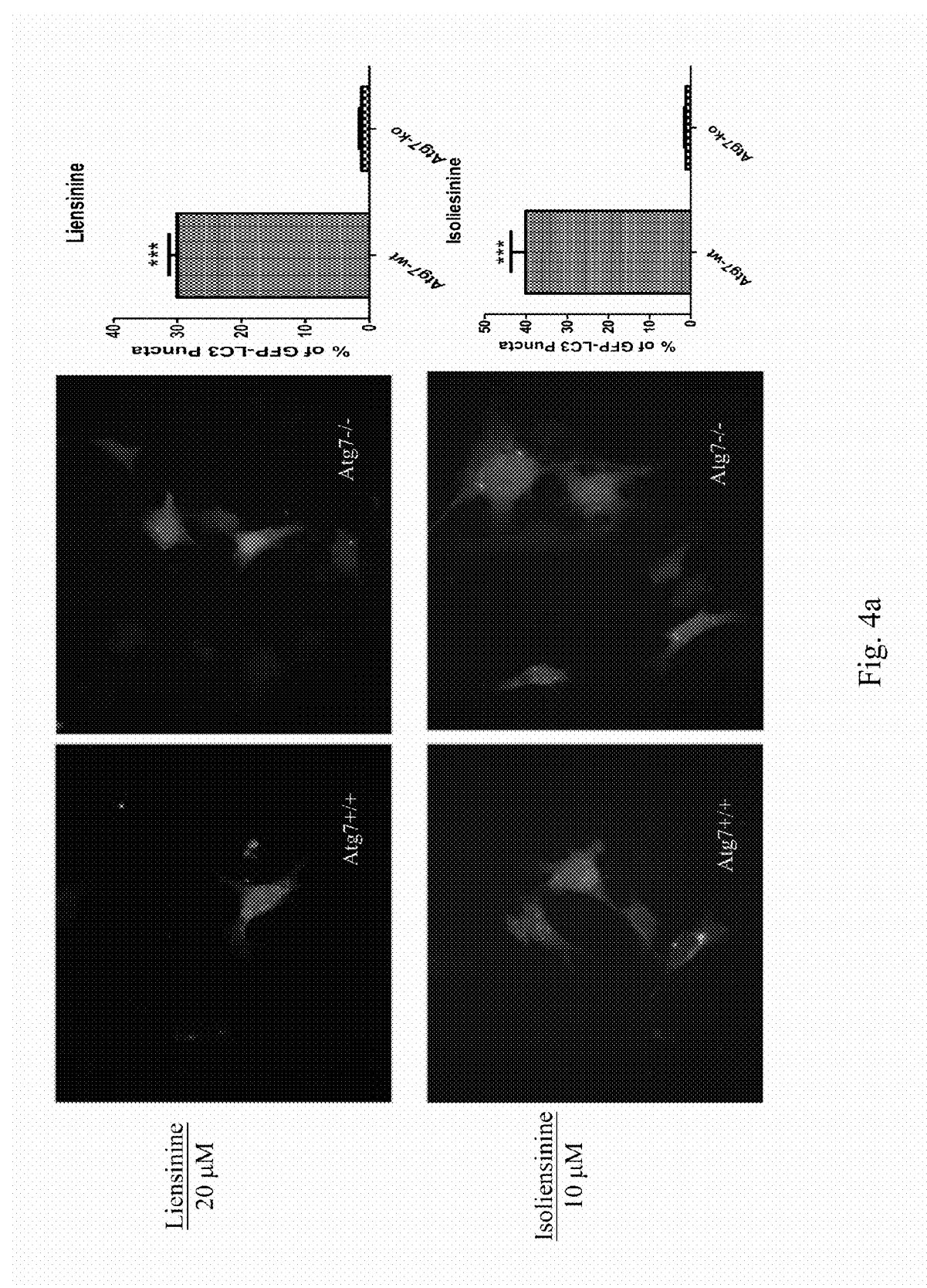
FIGS. 4a to 4c show that liensinine, isoliensinine, dauricine, cepharanthine, hernandezine and thalidezine-induced autophagy are dependent on the presence of autophagy-related gene 7 (Atg7).
Figure 4B:
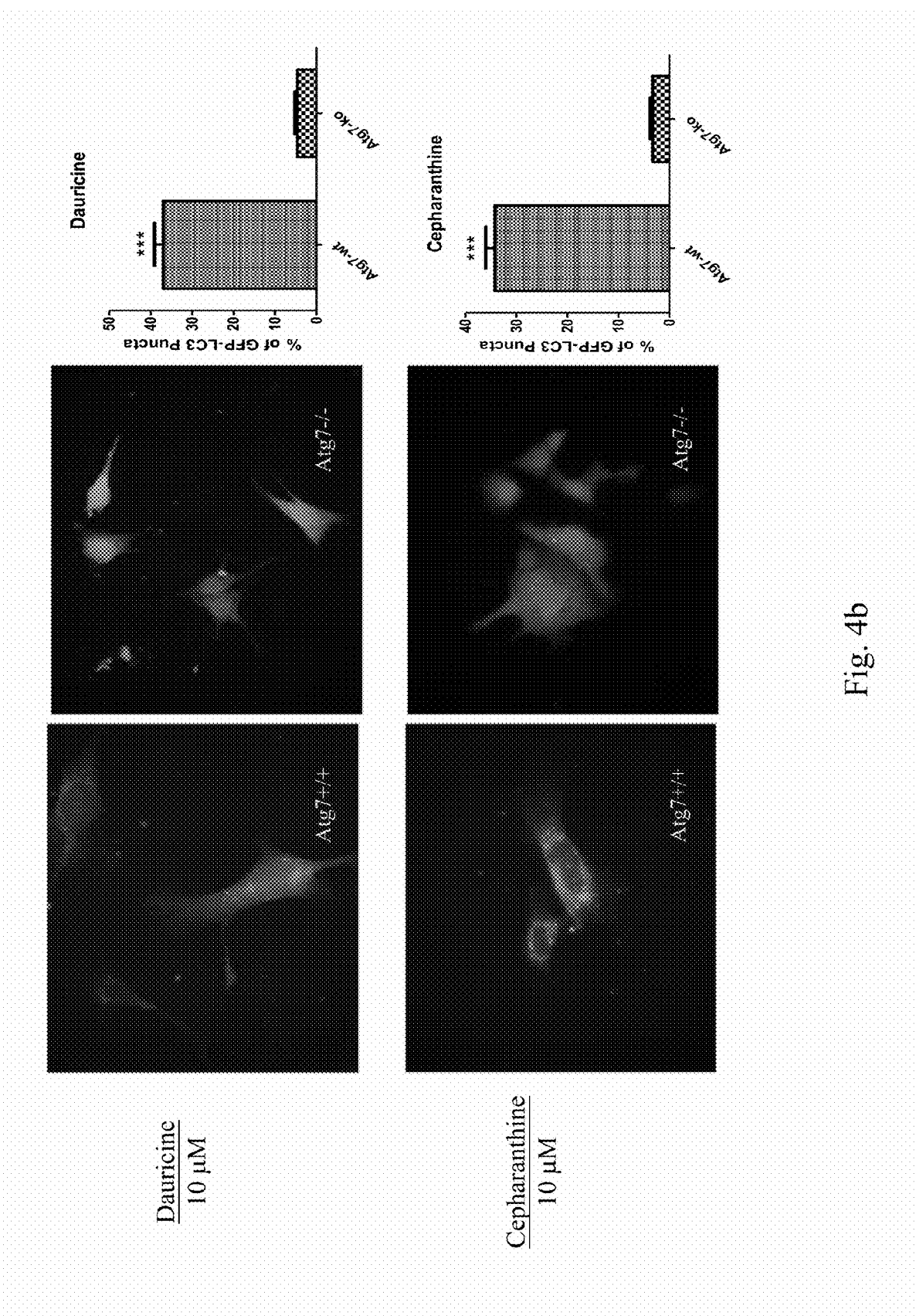
Figure 4C:
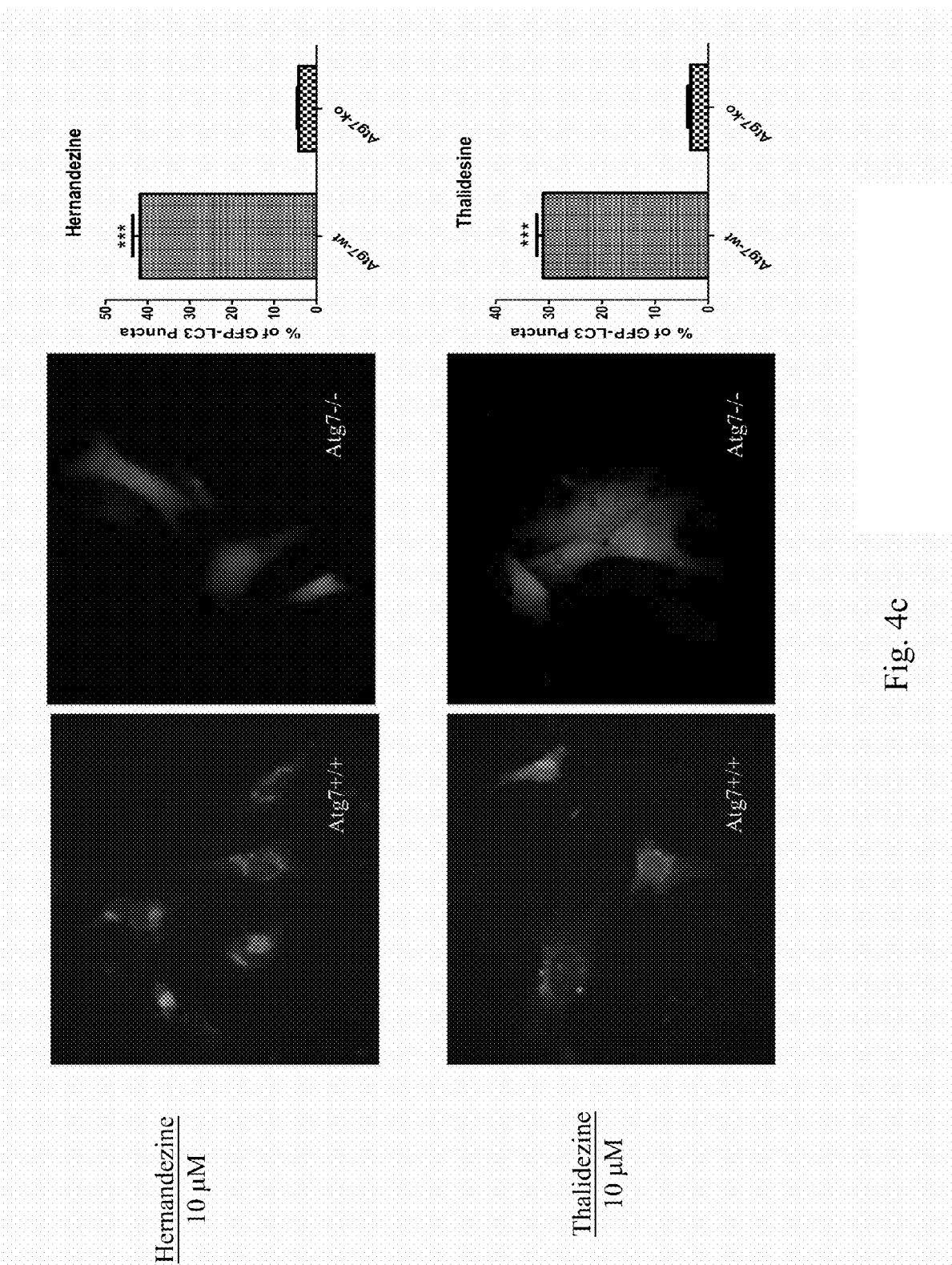

3.2 Results:

Liensinine, isoliensinine, dauricine, cepharanthine, hernandezine and thalidezine were found to induce GFP-LC3 puncta formation in wild type Atg7 cells but not in Atg7-knockout (Atg7-ko or Atg7−/−) mouse embryonic fibroblasts, as shown in FIGS. 4a to 4c.

3.3 Conclusion:

Liensinine, isoliensinine, dauricine, cepharanthine, hernandezine and thalidezine work as the novel autophagy enhancers which depend on autophagy related gene, Atg7, for the induction of autophagy. In other words, the autophagy induced by the six aforementioned compounds was Atg-7 dependent.

Example 4

Study on Mechanism of Autophagy Induction

This example describes an in vitro study to demonstrate the mechanism and action of liensinine, isoliensinine, dauricine, cepharanthine, hernandezine and thalidezine during autophagy induction.

4.1 Detection of mTOR Signaling Marker Proteins.

HeLa cells treated with 20 μM of liensinine, 10 μM of isoliensinine, 10 μM of dauricine, 10 μM of cepharanthine, 10 μM of hernandezine and 10 μM of thalidezine were harvested and lysed in RIPA buffer (Cell Signaling). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with P-p70S6K, p70S6K, P-AMPK, AMPK and actin primary antibodies (1:1000) in TBST overnight at 4° C. respectively. After that, the membrane was further incubated with HRP-conjugated secondary antibodies for 60 minutes. Finally, protein bands were visualized by using the ECL Western Blotting Detection Reagents (Invitrogen).

4.2 Quantification of Liensinine, Isoliensinine, Dauricine, Cepharanthine, Hernandezine and Thalidezine-Mediated Autophagy in the Presence of Specific Inhibitor.

GFP-LC3 puncta formation was quantified as previously described [15]. In brief, HeLa cells expressing GFP-LC3 were treated with indicated concentrations of liensinine, isoliensinine, dauricine, cepharanthine, hernandezine and thalidezine in the presence of AMPK inhibitor, compound C (CC, 5 μM), for 24 hours. The cells were then fixed in 4% paraformaldehyde for 20 minutes at room temperature and then rinsed with PBS. Slides were mounted with Fluor-Save™ mounting media (Calbiochem) and examined by fluorescence microscopy. To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields were scored.

4.3 Results.

Figure 5A:
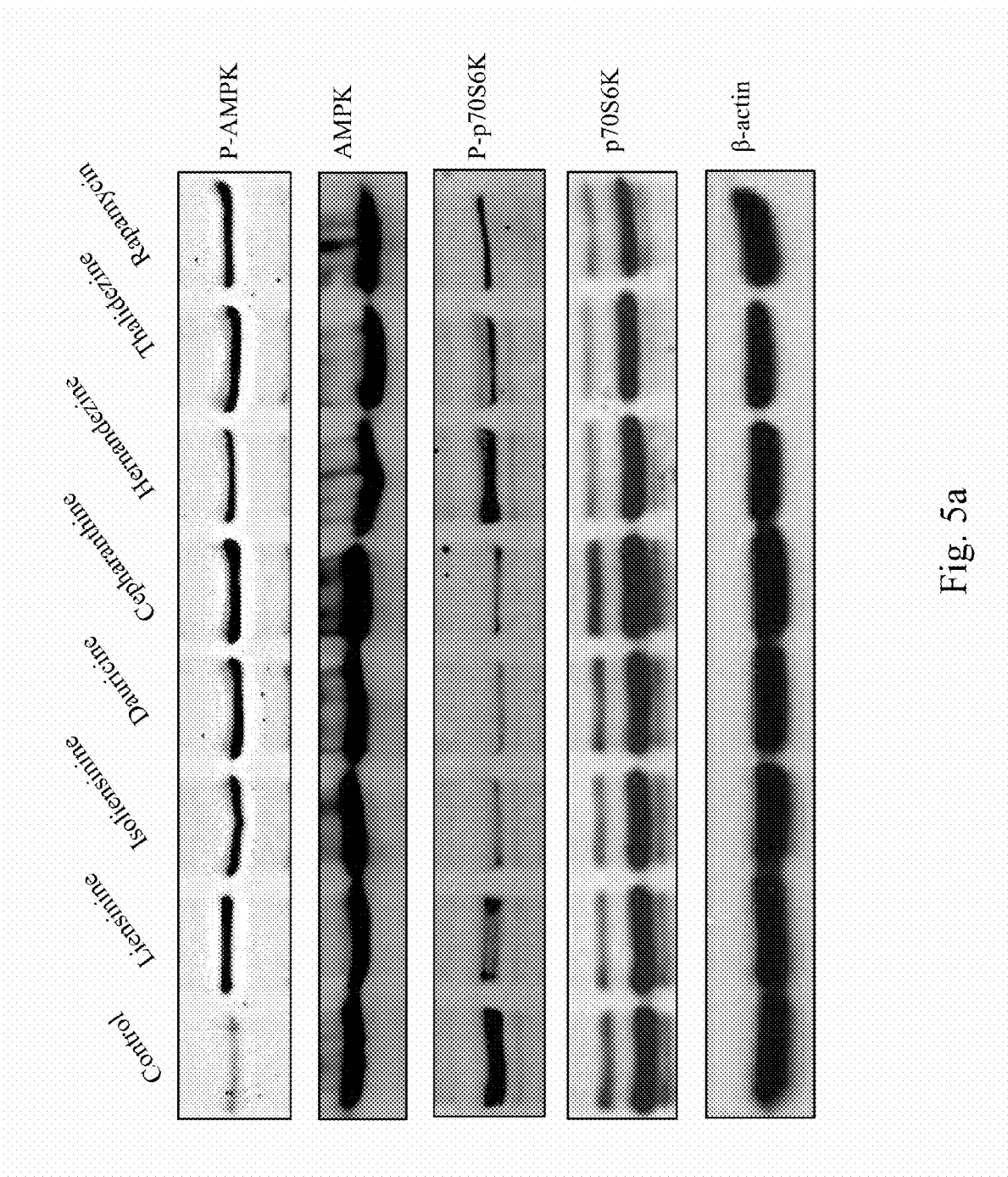
FIGS. 5a to 5b show that liensinine, isoliensinine, dauricine, cepharanthine, hernandezine and thalidezine activate autophagy through modulation of AMPK-mTOR signaling pathway.
Figure 5B:
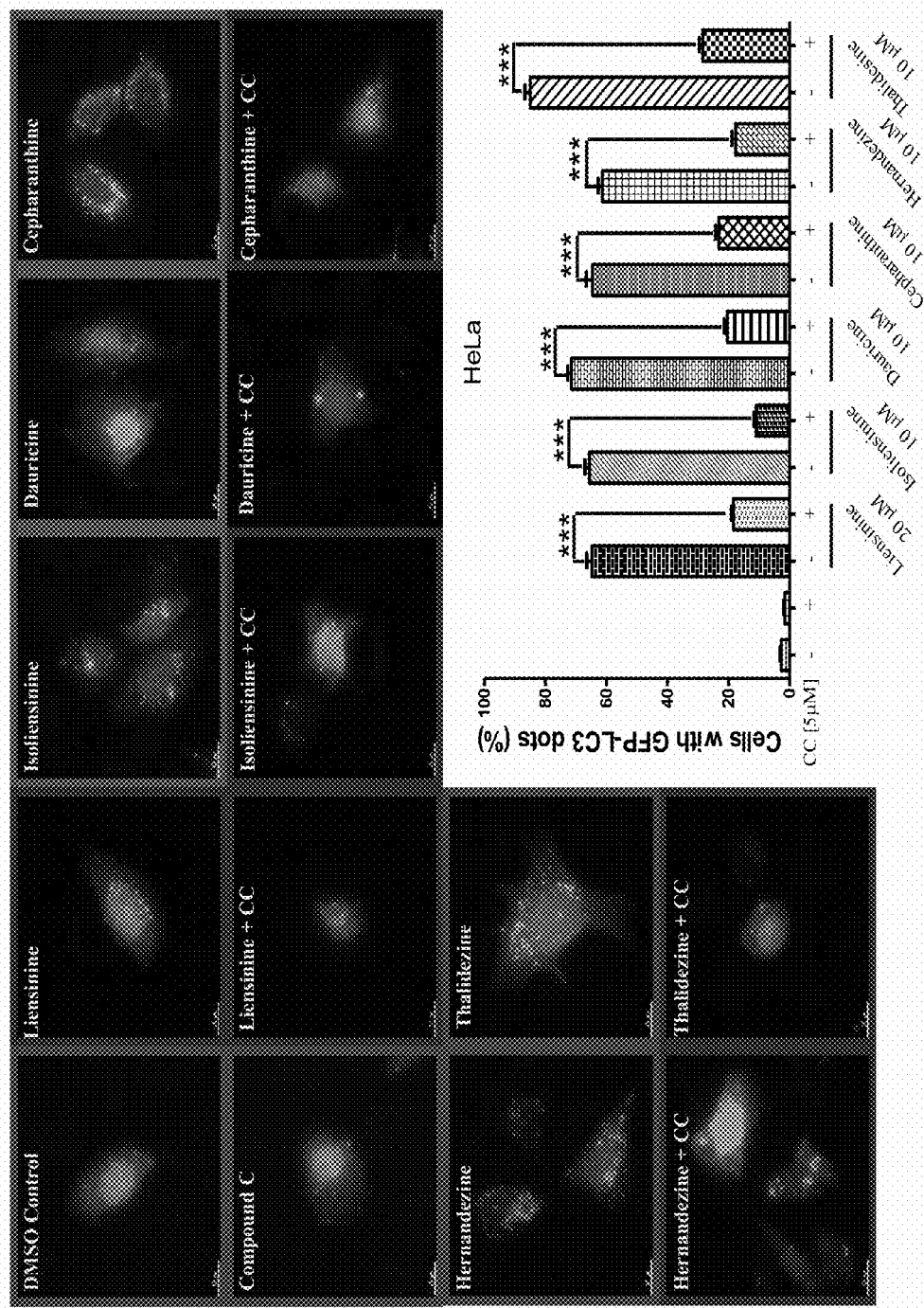

Liensinine, isoliensinine, dauricine, cepharanthine, hernandezine and thalidezine were found to activate the phosphorylation of AMPK as compared to DMSO control treatment as shown in FIG. 5a and this activation was also accompanied by a concomitant reduction in its downstream p70S6K phosphorylation. In order to confirm whether the AMPK signaling is involved in autophagy induced by liensinine, isoliensinine, dauricine, cepharanthine, hernandezine or thalidezine, specific AMPK inhibitor, compound C, was used in the study. Results showed that there was a significant reduction in the GFP-LC3 puncta formation induced by liensinine, isoliensinine, dauricine, cepharanthine, hernandezine or thalidezine in HeLa cells treated with the presence of AMPK inhibitor (Compound C), as shown in FIG. 5b, suggesting that the AMPK signaling is required for autophagy induction by these alkaloid compounds.

4.4 Conclusion.

Liensinine, isoliensinine, dauricine, cepharanthine, hernandezine and thalidezine are shown to induce autophagy via modulation of AMPK-mTOR signaling pathway.

Example 5

Study of Induction of Autophagic Cell Death in Cells

This example describes an in vitro study to demonstrate that liensinine, isoliensinine, dauricine, cepharanthine, hernandezine and thalidezine induce autophagic cell death in cells.

5.1 Cell Culture and Flow Cytometry Analysis.

Cell viability was measured using an annexin V staining kit (BD Biosciences, San Jose, Calif., USA). Briefly, Atg7 wild-type (Atg7 +/+ or Atg7-wt) and Atg7 deficient (Atg7 −/− or Atg7-ko) mouse embryonic fibroblasts (MEFs) were treated with the selected alkaloids for 24 h. Cells were then harvested and analysed by multiparametric flow cytometry using FITC-Annexin V and Propidium iodide staining (BD Biosciences, San Jose, Calif., USA) according to the manufacturer's instructions. Flow cytometry was then carried out using a FACSCalibur flow cytometer (BD Biosciences, San Jose, Calif., USA). Data acquisition and analysis was performed with CellQuest (BD Biosciences, San Jose, Calif., USA). Data were obtained from three independent experiments.

5.2 Results.

Figure 6A:
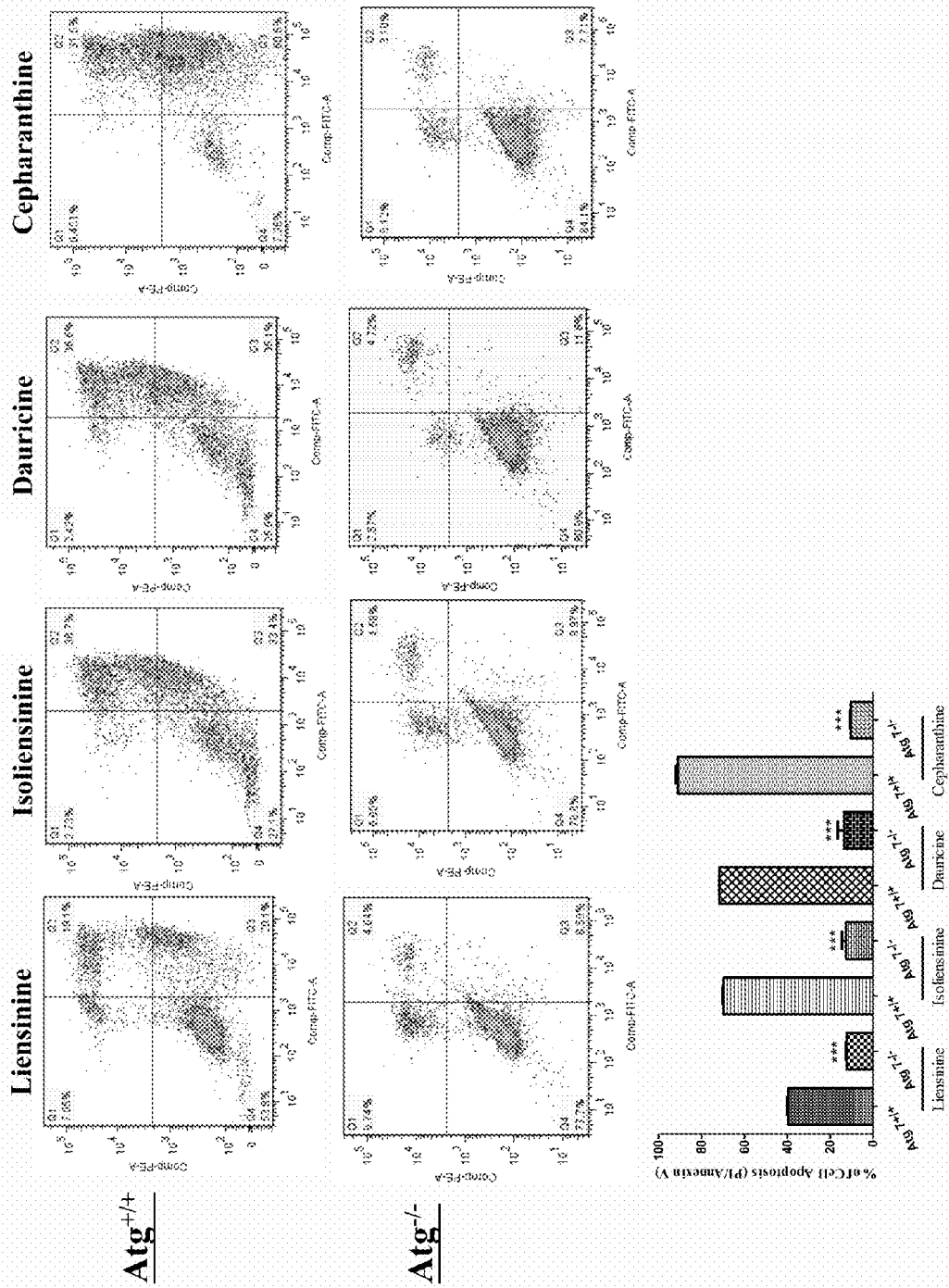
FIGS. 6a to 6c show that liensinine, isoliensinine, dauricine, cepharanthine, hernandezine and thalidezine are able to induce autophagic cell death in wild-type Atg7 cells, but not in Atg7 deficient cells.
Figure 6B:
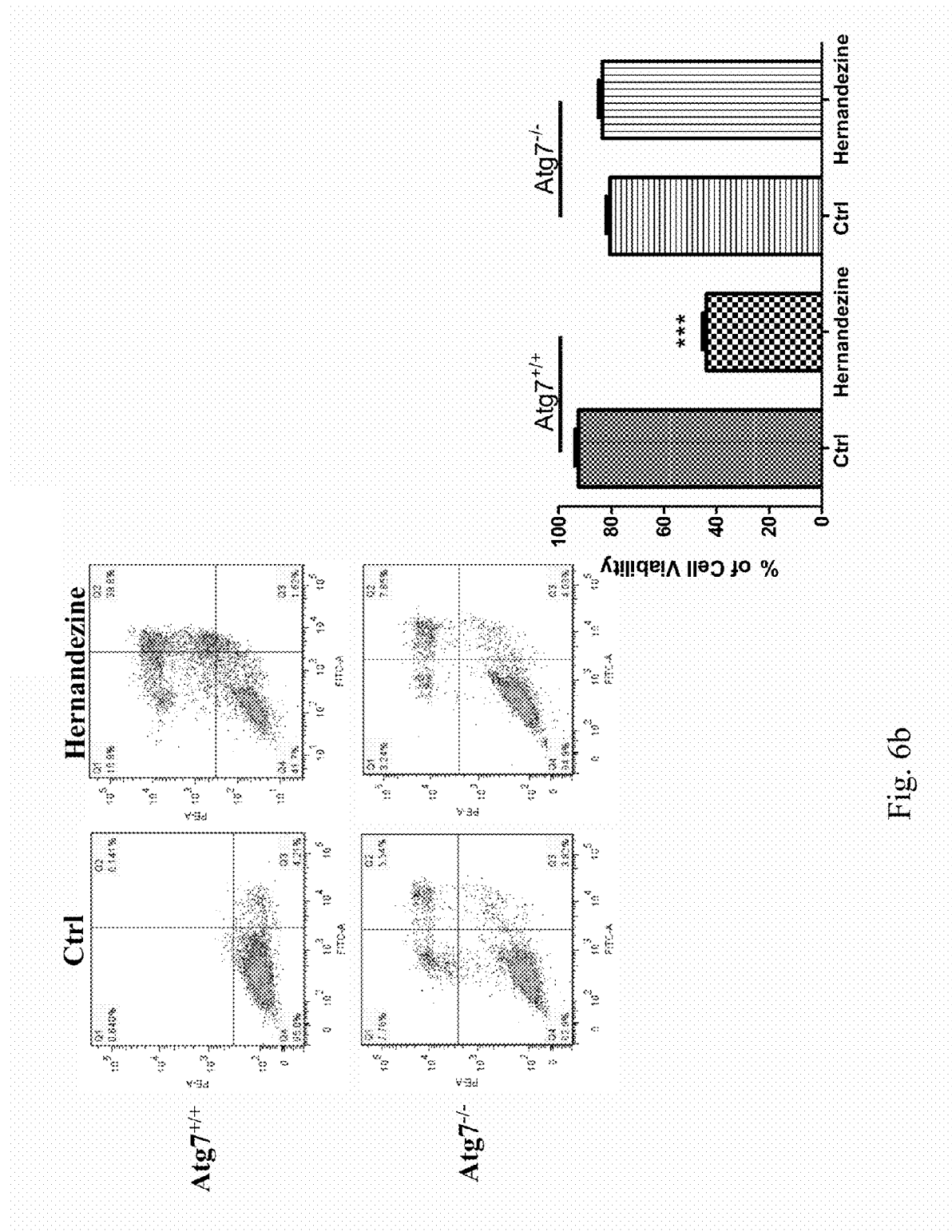
Figure 6C:
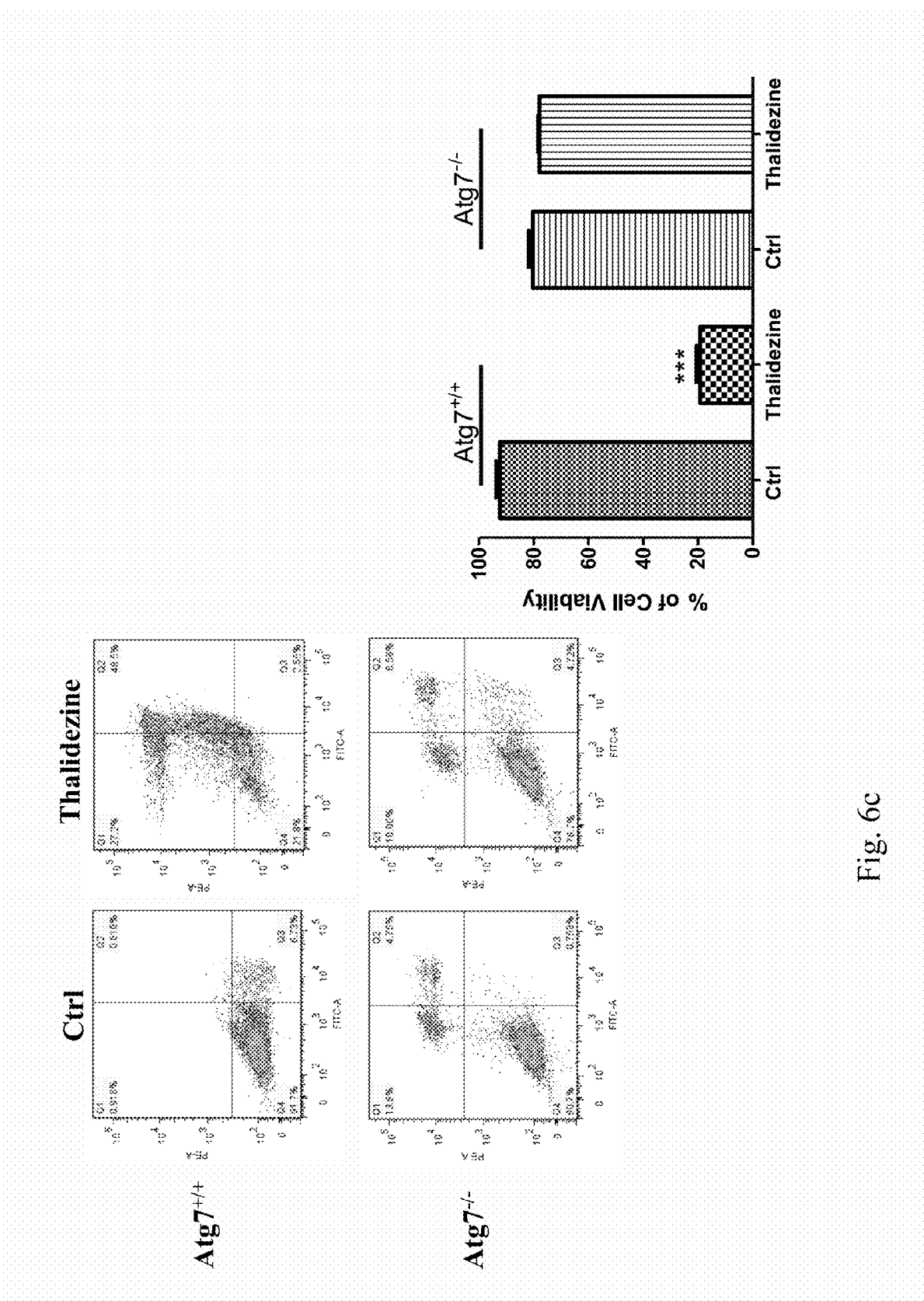
Figure 7E:
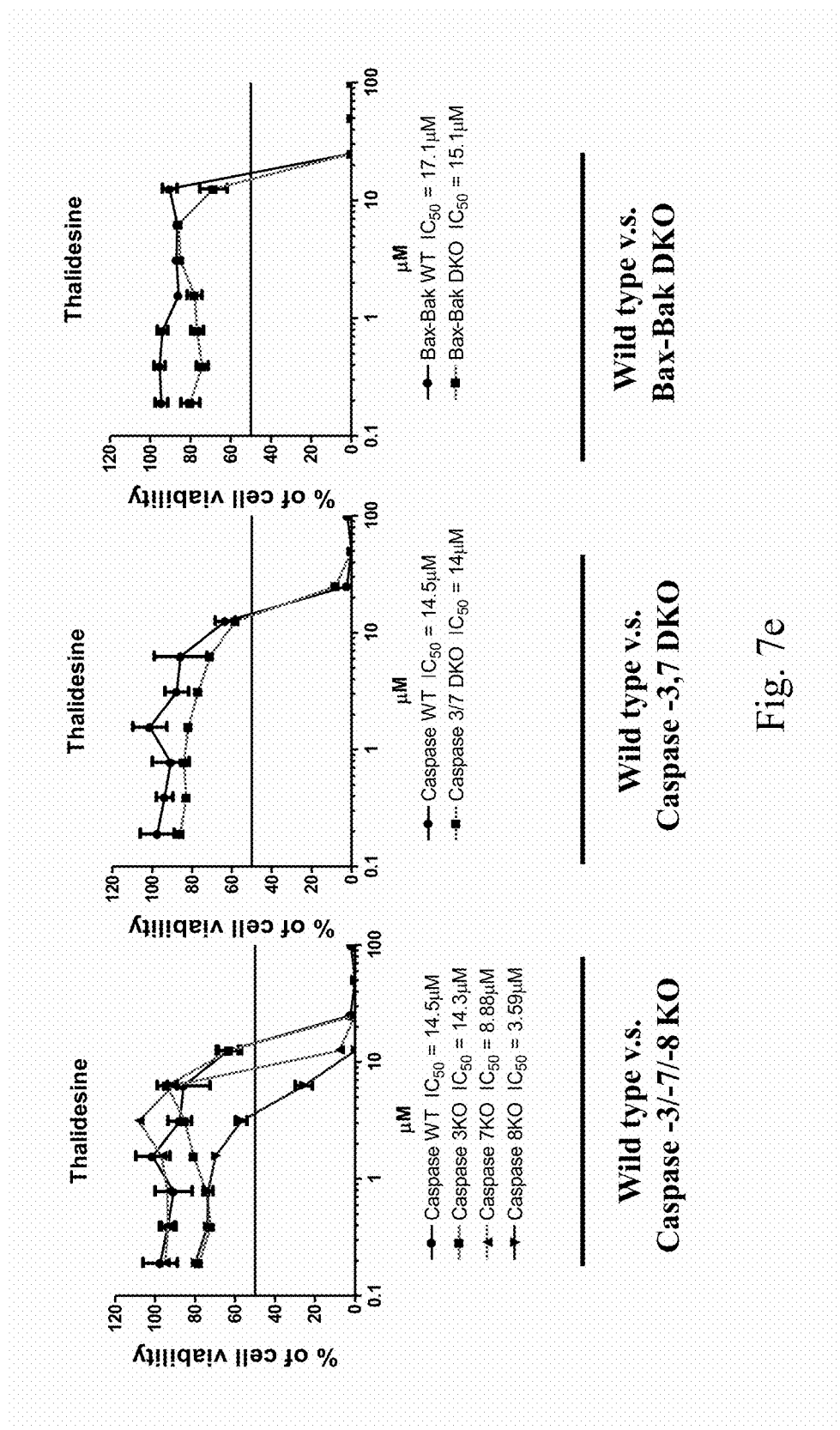

Among the six tested compounds, as shown in FIGS. 6a to 6c, all alkaloids are found to exhibit less cytotoxic effect to autophagy deficient cells (Atg7 −/− or Atg7-ko).

5.3 Conclusion.

The results suggest that liensinine, isoliensinine, dauricine, cepharanthine, hernandezine and thalidezine induce cell death or cell cytotoxicity via autophagy induction.

Example 6

Study on Study of Induction of Cell Cytotoxicity in Apoptosis-Resistant Cells

This example describes an in vitro study to demonstrate that isoliensinine, dauricine, cepharanthine, hernandezine and thalidezine potently induce cell cytotoxicity in apoptosis-resistant cells.

6.1 Cell Culture and Cytotoxicity Assay.

The test compounds of isoliensinine, dauricine, cepharanthine, hernandezine and thalidezine were dissolved in DMSO at a final concentration of 100 mmol/L and stored at −20° C. Cytotoxicity was assessed using the 3-(4,5-dimethylthiazol-2-yl)-2,5-diphenyltetrazolium bromide assay as previously described [25]. 2500 of caspase wild-type (caspase WT), caspase-3 deficient (caspase 3KO), caspase-7 deficient (caspase 7KO), caspase-3/-7 deficient (caspase 3/7 DKO), caspase-8 deficient (caspase 8KO), Bax-Bak wild-type (Bak-Bak WT) and Bax-Bak double knock out (Bak-Bak DKO) mouse embryonic fibroblasts (MEFs) were seeded on 96-well plates per well. After overnight pre-incubation, the cells were exposed to different concentrations of isoliensinine, dauricine, cepharanthine, hernandezine and thalidezine (0.039-100 μmol/L) for 3 days. Specifically, the following concentrations are used for all of the above alkaloids: 100, 50, 25, 12.5, 6.25, 3.125, 1.5625, 0.78, 0.39, 0.195, 0.079, 0.039 μmol/L. Subsequently, 10 μL of MTT reagents was added to each well and incubated at 37° C. for 4 hours, followed by the addition of 100 μL solubilization buffer (10% SDS in 0.01 mol/L HCl) and overnight incubation. Absorbance at 585 nm was determined from each well on the following day. The percentage of cell viability was calculated using the following formula: Cell viability (%)=Cells number treated/Cells number DMSO control×100. Data was obtained from three independent experiments.

6.2 Results.

Isoliensinine, dauricine, cepharanthine, hernandezine and thalidezine are found to exhibit similar cytotoxic effect on both wild-type and apoptosis-resistant cells, i.e. caspase-3/-7/-8 as compared to the caspase wild-type MEFs as shown in FIGS. 7a to 7e). In addition, from FIGS. 7a to 7e, similar cytotoxicity is also shown in Bax-Bak DKO apoptosis-resistant cells as compared to Bax-Bak wild-type MEFs, indicating that these alkaloid compounds are able to induce cell death in apoptosis-resistant cells.

6.3 Conclusion.

These findings suggest that isoliensinine, dauricine, cepharanthine, hernandezine and thalidezine are capable to induce cell cytotoxicity in apoptosis-resistant cancer cells.

Example 7

Study on Clearance of Mutant Huntingtin HDQ55/74

This example describes an in vitro study to demonstrate the clearance of mutant huntingtin HDQ55/74 by liensinine, isoliensinine, dauricine, cepharanthine, hernandezine and thalidezine.

7.1 Cell Culture and Cytotoxicity Assay.

For cell viability assay measured by crystal violet staining, PC-12 cells were incubated in 35 mm disc followed by the addition of liensinine, isoliensinine, dauricine, cepharanthine, hernandezine and thalidezine at 5-10 μM for 24 h. The cells were then incubated with crystal violet for 10 minutes followed by a ddH$_2$O wash. Images of the stained cells were captured by CCD digital camera Spot RT3™ under the Nikon ECLIPSE 80 microscope with 4× magnification. Cell viability was quantified by dissolving stained cells in 10% acetic acid (200 μL/well). The colorimetric reading of the solute mixture was then determined by spectrophotometer at OD 560 nm. The percentage of cell viability was calculated using the following formula: Cell viability (%)=Cells number$_{treated}$/Cells number$_{DMSO\ control}$×100. Data was obtained from three independent experiments.

7.2 Removal of Mutant Huntingtin.

PC 12 cells were transfected transiently with EGFP-HDQ55/74 plasmids for 24 h using Lipofectamine Plus LTX reagent (Invitrogen) according to the manufacturer's protocol. The transfected cells were then treated with liensinine, isoliensinine, dauricine, cepharanthine, hernandezine and thalidezine for 24 h. The removal of mutant huntingtin, (HDQ55 & HDQ74) was then quantitated by immunoblotting with antibody against EGFP or by immunocytochemistry under fluorescence microscopy.

7.3 Results.

Figure 8A:
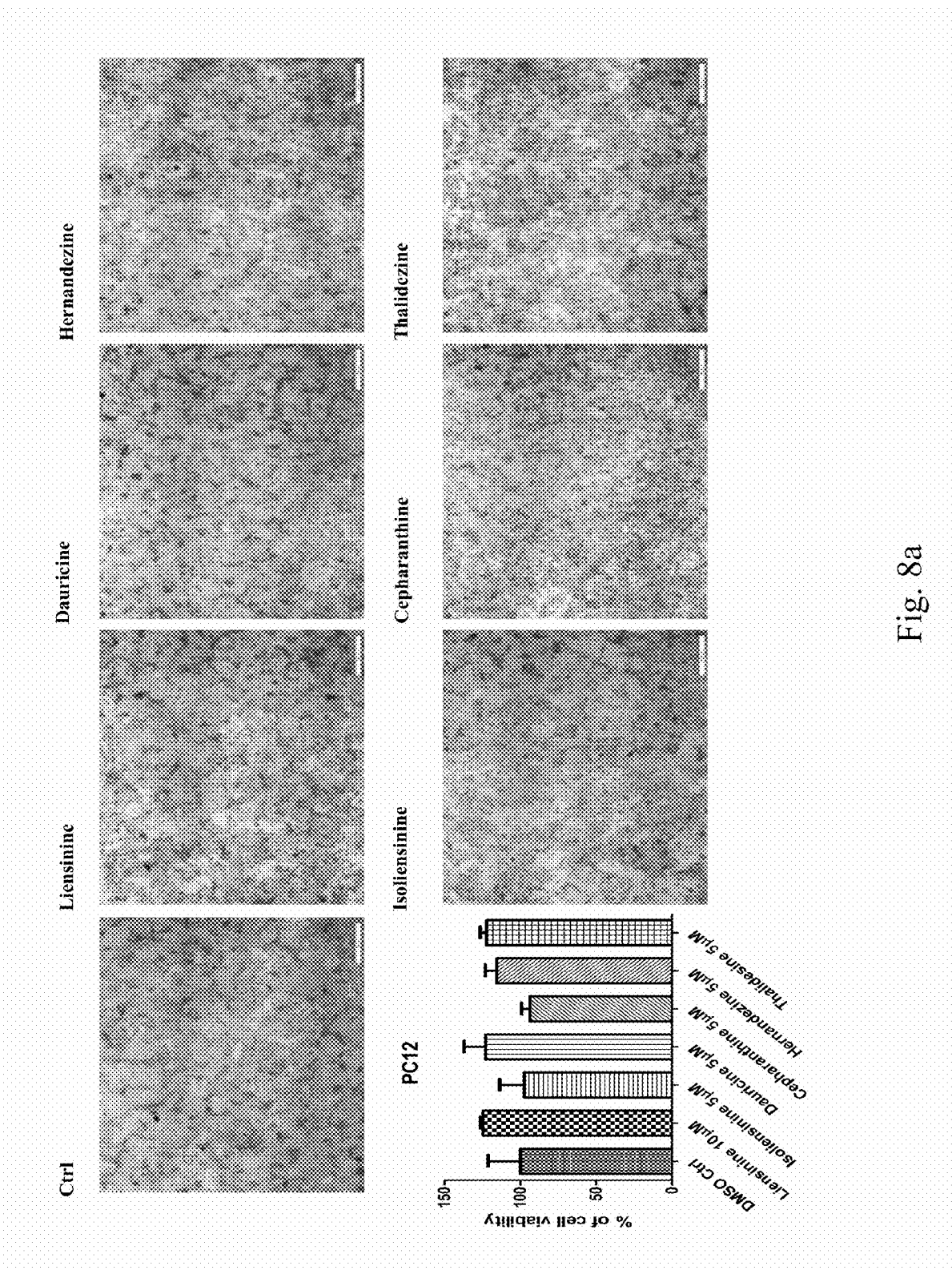
FIGS. 8a to 8c show the cell cytotoxicity and clearance of HTT mutant HDQ55/74 of liensinine, isoliensinine, dauricine, cepharanthine, hernandezine and thalidezine.
Figure 8B:
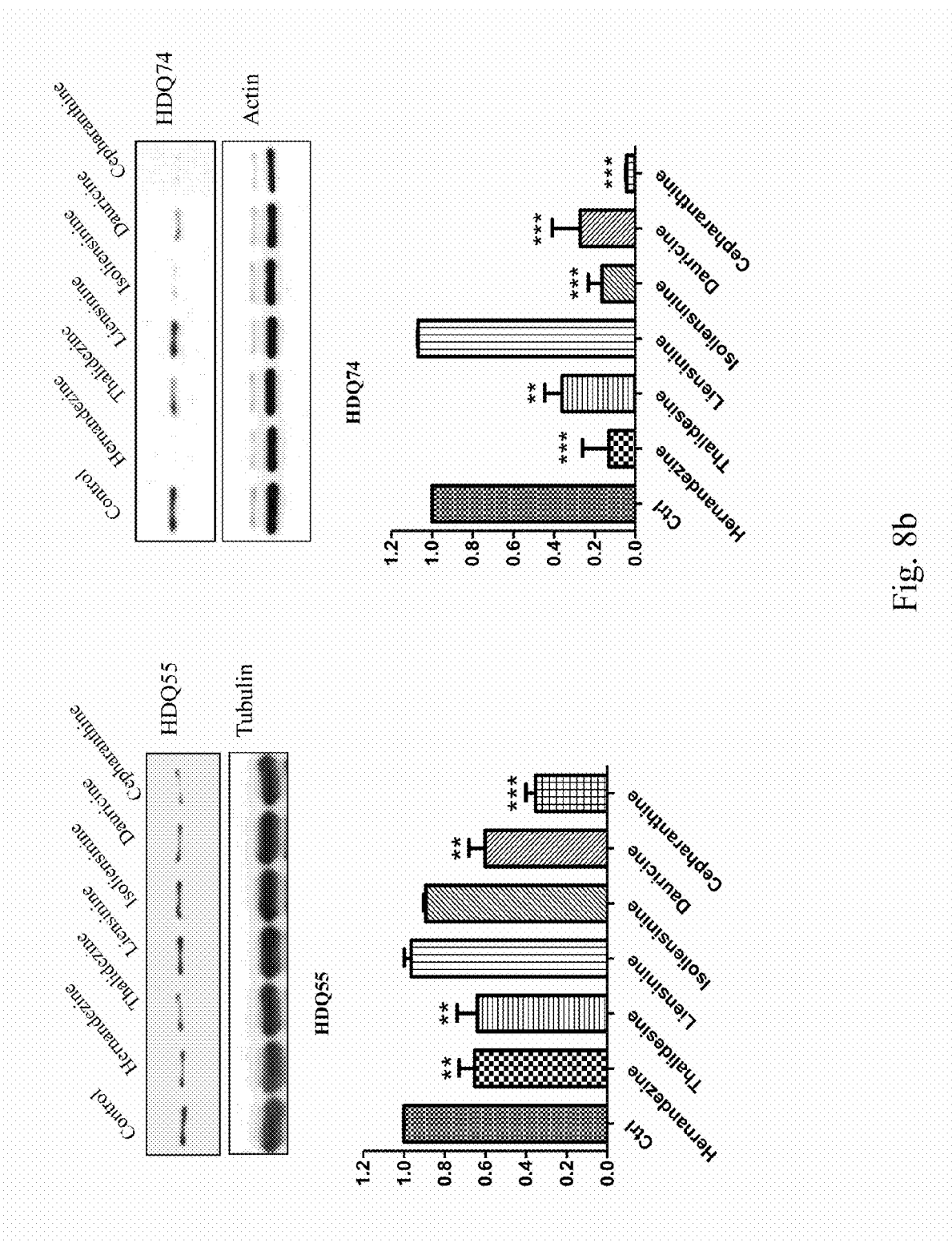
Figure 8C:
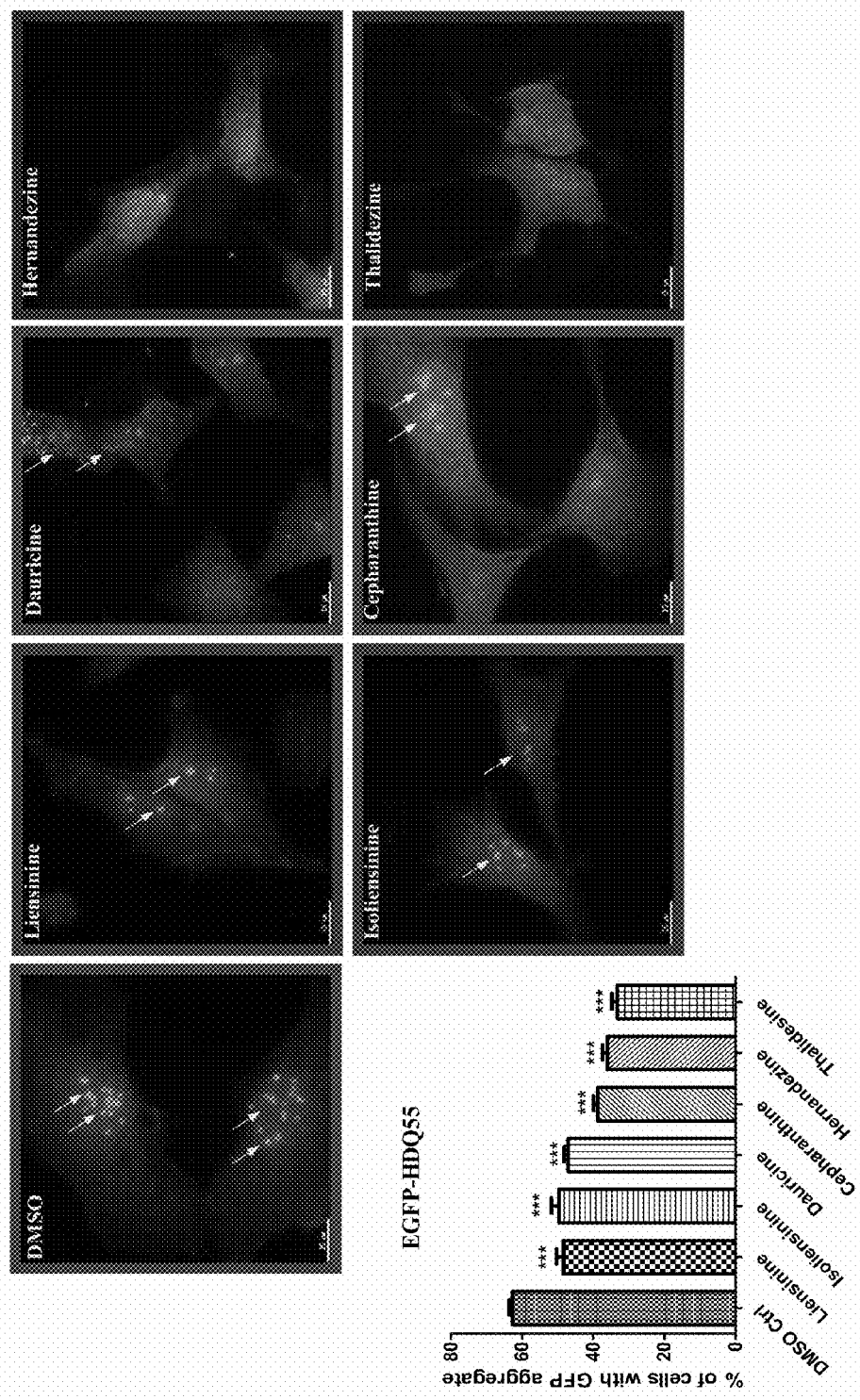

As shown in FIG. 8a, liensinine, isoliensinine, dauricine, cepharanthine, hernandezine and thalidezine exhibit no toxicity in PC 12 at 5-10 μM. In addition, 5-10 μM of liensinine, isoliensinine, dauricine, cepharanthine, hernandezine and thalidezine enhanced the clearance of overexpressed EGFP-tagged mutant huntingtin (HDQ55, HDQ74) with 55 and 74 CAG repeats as measured by immunoblotting against EGFP antibody as shown in FIG. 8b. Concomitantly, fluorescence imaging as illustrated in FIG. 8c further revealed that the six aforesaid compounds significantly reduced the formed mutant huntingtin aggregate (HDQ55) in PC 12 cells.

7.4 Conclusion.

Liensinine, isoliensinine, dauricine, cepharanthine, hernandezine and thalidezine may work as a novel neuroprotective agent through accelerating the clearance of mutant huntingtin.

The present invention relates to the identification of a group of novel autophagy enhancers, namely, liensinine, isoliensinine, dauricine, cepharanthine, hernandezine and thalidezine, which are isolated from Chinese medicinal herbs, *Nelumbo nucifera* (liensinine and isoliensinine), *Asiatic Moonseed Rhizome* (dauricine), *Stephania cepharantha* (cepharanthine), *Thalictrum hernandezii* (hernandezine) and *Thalictrum podocarpum Humb* (thalidezine) respectively. The invention also covers the anti-cancer effect of the above alkaloid compounds through induction of autophagic cell death in a panel of cancer cells and apoptosis-resistant cells. In addition, the invention further covers the neuroprotective effect of the above compounds on neuronal cells via enhancing the clearance of mutant huntingtin.

In one embodiment of the present invention, liensinine, isoliensinine, dauricine, cepharanthine, hernandezine and thalidezine exhibit significant cytotoxic effect towards a panel of cancer cells, but not in human normal liver LO2 cells. In the further embodiment of the present invention, liensinine, isoliensinine, dauricine, cepharanthine, hernandezine and thalidezine exhibit specific cytotoxic effect toward human cancer cells.

In one embodiment of the present invention, liensinine, isoliensinine, dauricine, cepharanthine, hernandezine and thalidezine are the novel autophagy enhancers and never be reported before. In the further embodiment of the present invention, liensinine, isoliensinine, dauricine, cepharanthine, hernandezine and thalidezine are capable to induce autophagy in a panel of cancer and normal cells, and animals.

In one embodiment of the present invention, autophagy induced liensinine, isoliensinine, dauricine, cepharanthine, hernandezine or thalidezine is dependent on autophagy-related gene 7 (Atg7)). In the further embodiment of the present invention, liensinine, isoliensinine, dauricine, cepharanthine, hernandezine and thalidezine are capable to induce autophagy in Atg7 dependent manner.

In one embodiment of the present invention, liensinine, isoliensinine, dauricine, cepharanthine, hernandezine and thalidezine induce autophagy via activation of AMP-activated protein kinase (AMPK) and inhibition of mammalian target of rapamycin (mTOR) signaling. In the further embodiment of the present invention, liensinine, isoliensinine, dauricine, cepharanthine, hernandezine and thalidezine are capable to induce autophagy via modulation of AMPK-mTOR signaling pathway.

In one embodiment of the present invention, liensinine, isoliensinine, dauricine and thalidezine are found to exhibit less cytotoxicity in autophagy deficient cells (Atg7−/−), indicating that liensinine, isoliensinine, dauricine and thalidezine are able to induce autophagic cell death in wild-type Atg7 cells. In the further embodiment of the present invention, liensinine, isoliensinine, dauricine and thalidezine are capable to induce autophagic cell death mechanism in Atg7 containing cancer cells.

In another embodiment of the present invention, isoliensinine, dauricine, cepharanthine, hernandezine and thalidezine exhibit significant cytotoxic effect towards a panel of apoptosis-resistant cells. In the further embodiment of the present invention, isoliensinine, dauricine, cepharanthine, hernandezine and thalidezine exhibit potent cytotoxic effect towards apoptosis-resistant cancer cells.

In another embodiment of the present invention, liensinine, isoliensinine, dauricine, cepharanthine, hernandezine and thalidezine enhance the clearance of mutant huntingtin HDQ55/74 in PC12 cells. In the further embodiment of the present invention, liensinine, isoliensinine, dauricine, cepharanthine, hernandezine and thalidezine are capable to enhance the clearance of mutant huntingtin.

The preferred embodiment of the present invention, liensinine, isoliensinine, dauricine, cepharanthine, hernandezine and thalidezine could be developed as novel anticancer and neuroprotective agents for patients with cancers or neurodegenerative diseases.

In another embodiment, the neurodegenerative diseases can be selected from Alzheimer's disease, Parkinson's disease, Huntington's disease, amyotrophic lateral sclerosis, ataxia telangiectasia, spinocerebellar atrophy and multiple sclerosis.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

REFERENCES

1. Levine, B., and G. Kroemer. 2008. Autophagy in the pathogenesis of disease. Cell 132:27-42.
2. Pallauf, K., and G. Rimbach. Autophagy, polyphenols and healthy ageing. Ageing Res Rev 12:237-252.
3. Rubinsztein, D. C., J. E. Gestwicki, L. O. Murphy, and D. J. Klionsky. 2007. Potential therapeutic applications of autophagy. Nat Rev Drug Discov 6:304-312.
4. Ravikumar, B., R. Duden, and D. C. Rubinsztein. 2002. Aggregate-prone proteins with polyglutamine and polyalanine expansions are degraded by autophagy. Hum Mol Genet 11:1107-1117.
5. Ravikumar, B., C. Vacher, Z. Berger, J. E. Davies, S. Luo, L. G. Oroz, F. Scaravilli, D. F. Easton, R. Duden, C. J. O'Kane, and D. C. Rubinsztein. 2004 Inhibition of mTOR induces autophagy and reduces toxicity of polyglutamine expansions in fly and mouse models of Huntington disease. Nat Genet 36:585-595.
6. Webb, J. L., B. Ravikumar, J. Atkins, J. N. Skepper, and D. C. Rubinsztein. 2003. Alpha-Synuclein is degraded by both autophagy and the proteasome. J Biol Chem 278:25009-25013.
7. Berger, Z., B. Ravikumar, F. M. Menzies, L. G. Oroz, B. R. Underwood, M. N. Pangalos, I. Schmitt, U. Wullner, B. O. Evert, C. J. O'Kane, and D. C. Rubinsztein. 2006. Rapamycin alleviates toxicity of different aggregate-prone proteins. Hum Mol Genet 15:433-442.
8. Rubinsztein, D. C., G. Marino, and G. Kroemer. Autophagy and aging. Cell 146:682-695.
9. Sarkar, S., E. O. Perlstein, S. Imarisio, S. Pineau, A. Cordenier, R. L. Maglathlin, J. A. Webster, T. A. Lewis, C. J. O'Kane, S. L. Schreiber, and D. C. Rubinsztein. 2007. Small molecules enhance autophagy and reduce toxicity in Huntington's disease models. Nat Chem Biol 3:331-338.
10. Ravikumar, B., S. Sarkar, J. E. Davies, M. Futter, M. Garcia-Arencibia, Z. W. Green-Thompson, M. Jimenez-Sanchez, V. I. Korolchuk, M. Lichtenberg, S. Luo, D. C. Massey, F. M. Menzies, K. Moreau, U. Narayanan, M. Renna, F. H. Siddigi, B. R. Underwood, A. R. Winslow, and D. C. Rubinsztein. Regulation of mammalian autophagy in physiology and pathophysiology. Physiol Rev 90:1383-1435.
11. Mathew, R., S. Kongara, B. Beaudoin, C. M. Karp, K. Bray, K. Degenhardt, G. Chen, S. Jin, and E. White. 2007. Autophagy suppresses tumor progression by limiting chromosomal instability. Genes Dev 21:1367-1381.
12. Liang, X. H., S. Jackson, M. Seaman, K. Brown, B. Kempkes, H. Hibshoosh, and B. Levine. 1999. Induction of autophagy and inhibition of tumorigenesis by beclin 1. Nature 402:672-676.
13. Kondo, Y., T. Kanzawa, R. Sawaya, and S. Kondo. 2005. The role of autophagy in cancer development and response to therapy. Nat Rev Cancer 5:726-734.
14. Hoyer-Hansen, M., L. Bastholm, I. S. Mathiasen, F. Elling, and M. Jaattela. 2005. Vitamin D analog EB1089 triggers dramatic lysosomal changes and Beclin 1-mediated autophagic cell death. Cell Death Differ 12:1297-1309.
15. Law, B. Y., M. Wang, D. L. Ma, F. Al-Mousa, F. Michelangeli, S. H. Cheng, M. H. Ng, K. F. To, A. Y. Mok, R. Y. Ko, S. K. Lam, F. Chen, C. M. Che, P. Chiu, and B. C. Ko. Alisol B, a novel inhibitor of the sarcoplasmic/endoplasmic reticulum Ca(2+) ATPase pump, induces autophagy, endoplasmic reticulum stress, and apoptosis. Mol Cancer Ther 9:718-730.
16. Wong, V. K., T. Li, B. Y. Law, E. D. Ma, N. C. Yip, F. Michelangeli, C. K. Law, M. M. Zhang, K. Y. Lam, P. L. Chan, and L. Liu. Saikosaponin-d, a novel SERCA inhibitor, induces autophagic cell death in apoptosis-defective cells. Cell Death Dis 4:e720.
17. Lu, J. J., J. L. Bao, X. P. Chen, M. Huang, and Y. T. Wang. Alkaloids isolated from natural herbs as the anti-cancer agents. Evid Based Complement Alternat Med 2012:485042.
18. Meng, L. H., H. Zhang, L. Hayward, H. Takemura, R. G. Shao, and Y. Pommier 2004. Tetrandrine induces early G1 arrest in human colon carcinoma cells by down-regulating the activity and inducing the degradation of G1-S-specific cyclin-dependent kinases and by inducing p53 and p21Cip1. Cancer Res 64:9086-9092.
19. Wang, N., Y. Feng, M. Zhu, C. M. Tsang, K. Man, Y. Tong, and S. W. Tsao. Berberine induces autophagic cell death and mitochondrial apoptosis in liver cancer cells: the cellular mechanism. J Cell Biochem 111:1426-1436.
20. Ho, Y. T., J. S. Yang, T. C. Li, J. J. Lin, J. G. Lin, K. C. Lai, C. Y. Ma, W. G. Wood, and J. G. Chung. 2009. Berberine suppresses in vitro migration and invasion of human SCC-4 tongue squamous cancer cells through the inhibitions of FAK, IKK, NF-kappaB, u-PA and MMP-2 and -9. Cancer Lett 279:155-162.
21. Li, W., Y. Shao, L. Hu, X. Zhang, Y. Chen, L. Tong, C. Li, X. Shen, and J. Ding. 2007. BM6, a new semi-synthetic vinca alkaloid, exhibits its potent in vivo anti-tumor activities via its high binding affinity for tubulin and improved pharmacokinetic profiles. Cancer Biol Ther 6:787-794.
22. Huang, M., H. Gao, Y. Chen, H. Zhu, Y. Cai, X. Zhang, Z. Miao, H. Jiang, J. Zhang, H. Shen, L. Lin, W. Lu, and J. Ding. 2007. Chimmitecan, a novel 9-substituted camptothecin, with improved anticancer pharmacologic profiles in vitro and in vivo. Clin Cancer Res 13:1298-1307.
23. Lu, J. H., J. Q. Tan, S. S. Durairajan, L. F. Liu, Z. H. Zhang, L. Ma, H. M. Shen, H. Y. Chan, and M. Li. Isorhynchophylline, a natural alkaloid, promotes the degradation of alpha-synuclein in neuronal cells via inducing autophagy. Autophagy 8:98-108.
24. Kulkarni, S. K., and A. Dhir. Berberine: a plant alkaloid with therapeutic potential for central nervous system disorders. Phytother Res 24:317-324.
25. Wong, V. K., H. Zhou, S. S. Cheung, T. Li, and L. Liu. 2009. Mechanistic study of saikosaponin-d (Ssd) on suppression of murine T lymphocyte activation. J Cell Biochem 107:303-315.

What is claimed is:

1. A method of treating neurodegenerative disorder comprising:
administering an effective amount of an alkaloid to a subject in need thereof, wherein the alkaloid is thalidezine, and the neurodegenerative disorder is Huntington's disease caused by cells containing Mutant huntingtin HDQ55/54.

2. The method of claim 1, wherein the thalidezine is represented by the following formula (I):

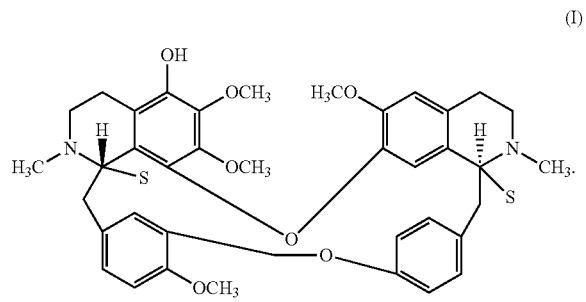

3. The method of claim 1, wherein the thalidezine is isolated from seed embryos of *Thalictrum podocarpum Humb*.

* * * * *